US009650389B2

(12) United States Patent
Cho et al.

(10) Patent No.: US 9,650,389 B2
(45) Date of Patent: May 16, 2017

(54) 8-OXOPROTOBERBERINE DERIVATIVE OR PHARMACEUTICALLY ACCEPTABLE SALT THEREOF, PREPARATION METHOD THEREFOR AND PHARMACEUTICAL COMPOSITION FOR PREVENTING OR TREATING DISEASES ASSOCIATED WITH ACTIVITY OF NFAT5, CONTAINING SAME AS ACTIVE INGREDIENT

(71) Applicants: Korea Research Institute of Chemical Technology, Daejeon (KR); The Catholic University of Korea Industry-Academic Cooperation Foundation, Seoul (KR)

(72) Inventors: Heeyeong Cho, Daejeon (KR); Hee-Jong Lim, Daejeon (KR); Ge Hyeong Lee, Daejeon (KR); Woo Kyu Park, Chungcheongbuk-do (KR); Hyeon Young Kim, Daejeon (KR); Dae Young Jeong, Daejeon (KR); Wan Uk Kim, Seoul (KR); Chul Soo Cho, Seoul (KR); Su Jung Park, Gyeonggi-do (KR); Eun Jin Han, Gyeongsangnam-do (KR)

(73) Assignees: Korea Research Institute of Chemical Technology, Daejeon (KR); The Catholic University of Korea Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 15/029,075

(22) PCT Filed: Dec. 30, 2014

(86) PCT No.: PCT/KR2014/013059
§ 371 (c)(1),
(2) Date: Apr. 13, 2016

(87) PCT Pub. No.: WO2015/102380
PCT Pub. Date: Jul. 9, 2015

(65) Prior Publication Data
US 2016/0251368 A1  Sep. 1, 2016

(30) Foreign Application Priority Data

Dec. 31, 2013 (KR) .................. 10-2013-0168600
Dec. 30, 2014 (KR) .................. 10-2014-0193586

(51) Int. Cl.
*C07D 491/153* (2006.01)
*A61K 31/4745* (2006.01)

(52) U.S. Cl.
CPC ...... *C07D 491/153* (2013.01); *A61K 31/4745* (2013.01)

(58) Field of Classification Search
None
See application file for complete search history.

(56) References Cited

U.S. PATENT DOCUMENTS

2010/0286396 A1* 11/2010 Chen .................. C07D 491/147
546/18
2013/0237556 A1  9/2013 Li et al. .................. 514/280

FOREIGN PATENT DOCUMENTS

KR   102007095279   9/2007

OTHER PUBLICATIONS

Cushman et al., J. Org. Chem. 1979, 44, 407-409.*
(Continued)

*Primary Examiner* — Karl J Puttlitz
(74) *Attorney, Agent, or Firm* — Licata & Tyrrell P.C.

(57) ABSTRACT

The preset invention relates to a novel 8-oxoprotoberberine derivative or a pharmaceutically acceptable salt thereof, a preparation method thereof, and a pharmaceutical compo-
(Continued)

sition for preventing or treating diseases associated with the activity of NFAT5 containing the same as an active ingredient. The novel 8-oxoproteoberberine derivative or the pharmaceutically acceptable salt thereof according to the present invention can be useful in a pharmaceutical composition for preventing or treating diseases associated with the activity of NFAT5, particularly rheumatoid arthritis or inflammatory diseases, since it is ascertained that the derivative or a pharmaceutically acceptable salt thereof has remarkably increased oral absorption compared with known protoberberine due to an improvement in the properties thereof, and inhibits the activity of NFAT5 and the secretion of inflammatory cytokines and reduces the expression of NAFT5 in mice with rheumatoid arthritis by directly inhibiting the transcription of NFT5.

7 Claims, 13 Drawing Sheets

(56) References Cited

OTHER PUBLICATIONS

Iwasa et al., J. Org. Chem. 1981, 46, 4744-4750.*
Chen et al. "Cytotoxicity and antihyperglycemic effect of minor constituents from *Rhizoma Coptis* in HepG2 cells" Fitoterapia 2012 83:67-73.
Skopalova et al. "Electrochemical oxidation of berberine and mass spectrometric identification of its oxidation products" Bioelectrochemistry 2012 87:15-20.

* cited by examiner

| parameter | IV, 5mg/kg | PO, 5mg/kg |
|---|---|---|
| $T_{max}$ (hr) | – | 2.66±1.15 |
| $C_{max}$(μg/mL) | – | 0.31±0.12 |
| $T_{1/2}$(hr) | 3.07±0.58 | 17.8±18.8 |
| $AUC_t$(μg-hr/mL) | 22.7±0.64 | 3.47±2.52 |
| $AUC_\infty$(μg-hr/mL) | 22.7±0.67 | 7.96±6.88 |
| CL(L/kg/hr) | 0.22±0.006 | – |
| $V_{ss}$ (L/kg) | 0.32±0.014 | – |
| $F_t$ (%) | – | 15.2 |

| parameter | IV, 5mg/kg | PO, 5mg/kg |
|---|---|---|
| $T_{max}$ (hr) | - | 4.67±2.31 |
| $C_{max}$(μg/mL) | - | 0.899±0.388 |
| $T_{1/2}$(hr) | 3.9±0.716 | 3.24±0.162 |
| $AUC_t$(μg-hr/mL) | 11.73±1.02 | 4.67±0.502 |
| $AUC_\infty$(μg-hr/mL) | 11.79±1.05 | 4.71±0.489 |
| CL(L/kg/hr) | 0.426±0.0378 | - |
| $V_{ss}$ (L/kg) | 0.971±0.173 | - |
| $F_t$(%) | - | 39.8 |

8-OXOPROTOBERBERINE DERIVATIVE OR PHARMACEUTICALLY ACCEPTABLE SALT THEREOF, PREPARATION METHOD THEREFOR AND PHARMACEUTICAL COMPOSITION FOR PREVENTING OR TREATING DISEASES ASSOCIATED WITH ACTIVITY OF NFAT5, CONTAINING SAME AS ACTIVE INGREDIENT

This patent application is the National Stage of International Application No. PCT/KR2014/013059 filed Dec. 30, 2014, which claims the benefit of priority from Korean Application No. 10-2014-0193586, filed Dec. 30, 2014 and Korean Application No. 10-2013-0168600, filed Dec. 31, 2013, each of which are herein incorporated by reference in their entirety.

BACKGROUND OF THE INVENTION

1. Field of the Invention

The present invention relates to a novel 8-oxoprotoberberine derivative or a pharmaceutically acceptable salt thereof, a preparation method thereof, and a pharmaceutical composition for preventing or treating diseases associated with the activity of NFAT5 containing the same as an active ingredient.

2. Description of the Related Art

Autoimmunity is a kind of immune response in human body, in which the body recognizes its own organ or tissue as an antigen invading from the outside so that it causes an immune response against it. Basically, the immune response is a system to defend human body against a foreign antigen such as a pathogen. However, when human body attacks its own organ or tissue because of autoimmunity, various diseases can be developed. Rheumatoid arthritis, systemic scleroderma, lupus erythematosus, atopic dermatitis, Behcet's disease, Sjogren's syndrome, multiple sclerosis, and Graves' hyperthyroidism are the examples of auto-immune disease.

Rheumatoid arthritis is an auto-immune disease that causes chronic and systemic inflammation in many tissues and organs. In this disease, the flexible synovial is mainly attacked to give pain and be transformed. If it is not properly treated, functions and motility will be damaged or lost. As the disease progresses, the joint is swollen owing to a huge amount of synovial fluid, the fibrous tissue (pannus) in the synovial is developed, the articular cartilage is destroyed, and inflammation is caused in ankylosis, lung, pericardium, pleura, and sclera. However, the cause of autoimmunity that causes rheumatoid arthritis has not been explained yet. Approximately 0.6% of adult population in USA is suffering from rheumatoid arthritis and the rate of female patient is 2~3 times higher than that of male patient (Non-Patent Reference 1).

The treatment of rheumatoid arthritis depends on the nonpharmacologic method such as physical therapy, orthoses and occupational therapy, and the pharmacologic method such as nutrition therapy, pain killer administration and anti-inflammatory drug administration. For the pharmacologic treatment, non-steroidal anti-inflammatory drug (NSAID) or disease-modified anti-rheumatic drug (DMARD) can be used. The said non-steroidal anti-inflammatory drug is effective by inhibiting the synthesis of prostaglandin by suppressing the enzyme activity of cyclooxygenase 2 (COX2) that is an important inflammation mediator, which is exemplified by diclofenac, piroxicam, indomethacin, meloxicam, celecoxib, rofecoxib, or lumiracoxib. However, these drugs cannot stop the progress of joint damage. The anti-rheumatoid drugs that can stop or delay the progress of the disease are exemplified by methotrexate, leflunomide, hydroxychloroquine, sulfasalazine, azathioprine, cyclophosphamide, and cyclosporine A. Anti-TNF-α antibody drug is also included in the category. As a low molecule drug, the JAK3 inhibitor Xeljanz (Tofacitinib, Pfizer) was first introduced in the market in 2012. Nevertheless, there are still numbers of non-reactive patients who do not respond to the conventional drugs, suggesting that unmet medical needs are still high, so that it is highly requested to develop a novel drug with a novel mechanism.

NFAT (nuclear factor of activated T cells) is a protein existing in cell membrane, which is activated by the $Ca^{2+}$ mobilization coupled cell surface receptor. NEAT protein is dephosphorylated by calcineurin that is the phosphatase activated by $Ca^{2+}$. The dephosphorylated NFAT migrates into the nucleus and induce the transcription of various cytokine genes including IL-2 necessary for the activation of T-cells.

In particular, NFAT5 (nuclear factor of activated T cells 5) is also called TonEBP (tonicity enhancer binding protein), OREBP, NFATL1, or NFATz. NFAT5 is the longest transcription regulator and displays a clear structural and functional difference from other transcription regulators {NFAT1 (NFATp, NFATc2), NFAT2 (NFATc, NFATc1), NFAT3 (NFATc4), NFAT4 (NFATx, NFATc3)} (Non-Patent References 2 and 3). NFAT5 is composed of approximately 1,500 amino acids and is expressed in almost every tissue, particularly displays a high expression in the kidney, lung, pituitary gland, placenta, testis, and thymus of a fetus characterized by active metabolism and aggressive development (Non-Patent Reference 4). NFAT5 does not have a calcineurin domain, suggesting that it is not directly affected by the calcium concentration. In a hypertonic solution with the increased osmotic pressure, NFAT5 is activated by osmostress and maintains homeostasis. The NFAT5 activated in T cells binds to CD24 promoter to increase the transcription of CD24, by which the amplification of T cells is induced.

ROS (reactive oxygen species) and p38 MAPK are the factors associated with NFAT5 upstream. It was previously reported that ROS is associated with the activation of NFAT5 induced by TLR (Toll-like receptor) (Non-Patent Reference 5). NO (nitric oxide), a member of ROS family, is generated by iNOS (inducible nitric oxide synthase). NO induced by iNOS plays an important role in many diseases, particularly in inflammation response. The expression of iNOS is characteristically shown in many diseases, according to the previous report (Non-Patent Reference 6).

It was recently reported that NFAT5 is highly expressed in synovial fluid of patients with rheumatoid arthritis, one of auto-immune diseases, and increases the secretion of inflammatory cytokines such as IL-1β and TNF-α (Non-Patent Reference 7). It was observed that the cell proliferation, angiogenesis, or cell migration was significantly reduced in NFAT5 knocked-down synovial cells or vascular cells (HUVEC) by using siRNA. In the NFAT5(+/−) mouse, inflammation in the joint was significantly reduced. Therefore, it is suggested that a compound that can inhibit the activity of NFAT5 can be a promising candidate for the novel treating agent for improving rheumatoid arthritis.

Berberine is a quaternary ammonium salt of isoquinoline alkaloid, which is known as an herbal medicine included in golden thread. It has been reported that berberine has the anti-cancer, anti-obesity, and anti-diabetic effect. Berberine is the active ingredient of the natural digestive 'Jungrowhan' which has the activities of inhibiting enterobacteria, anti-convulsive/sedative, preventing atherosclerosis, anti-inflammatory, choleretic, and promoting the secretion of pancreatic juice.

It was observed that protoberberine, a berberine derivative wherein various substituents are inserted in the 13$^{th}$ site of berberine with displaying remarkably improved NFAT5 inhibiting effect and COX enzyme inhibiting effect, was excellent in inhibiting inflammation in arthritis animal model. However, the said protoberberine has a low solubility so that it is not absorbed well through oral-administration, suggesting that it is hard to be developed as an oral-preparation.

The present inventors were fully aware of that a novel drug with a novel mechanism is necessary to cope with the drug-resistance since arthritis or auto-immune disease is the kind of disease that requires a long-term treatment and also recognized that an oral-preparation is preferred over an injection. Therefore, in the course of study to develop a compound that has NFAT5 inhibiting effect and can be orally administrated, the present inventors confirmed that the novel 8-oxoprotoberberine derivative has an excellent NFAT5 inhibiting effect and can be useful as an anti-rheumatoid arthritis agent suitable for the oral-administration, leading to the completion of the invention.

PRIOR ART REFERENCE

Non-Patent Reference

[Non-Patent Reference 1] Handout on Health: Rheumatoid Arthritis. National Institute of Arthritis and Musculoskeletal and Skin Diseases, April 2013;
[Non-Patent Reference 2] Biochem. Pharm. 72 (2006) 1597-1604;
[Non-Patent Reference 3] Nucleic Acids Res. 33 (2005) 3845-3854;
[Non-Patent Reference 4] J. Immunol. 165 (2000) 4884-4894;
[Non-Patent Reference 5] Eur J Immunol. 44 (2014) 2721-2736.
[Non-Patent Reference 6] Semin Cancer Biol. 15 (2005) 277-289.
[Non-Patent Reference 7] Arthritis and Rheumatism. 63 (2011) 1843-1852.

SUMMARY OF THE INVENTION

It is an object of the present invention to provide a novel 8-oxoprotoberberine derivative or a pharmaceutically acceptable salt thereof.

It is another object of the present invention to provide a method for preparing an 8-oxoprotoberberine derivative.

It is also an object of the present invention to provide a pharmaceutical composition comprising an 8-oxoprotoberberine derivative or a pharmaceutically acceptable salt thereof as an active ingredient.

It is further an object of the present invention to provide a pharmaceutical composition for the prevention or treatment of diseases associated with the activity of NFAT5 comprising an 8-oxoprotoberberine derivative or a pharmaceutically acceptable salt thereof as an active ingredient.

It is also an object of the present invention to provide a NFAT5 activity inhibitor comprising an 8-oxoprotoberberine derivative or a pharmaceutically acceptable salt thereof as an active ingredient.

It is also an object of the present invention to provide a health functional food composition for the prevention or improvement of diseases associated with the activity of NFAT5 comprising an 8-oxoprotoberberine derivative or a pharmaceutically acceptable salt thereof as an active ingredient.

It is also an object of the present invention to provide a method for preventing, improving, or treating diseases associated with the activity of NFAT5 containing the step of administering an effective dose of a 8-oxoprotoberberine derivative or a pharmaceutically acceptable salt thereof to a subject.

It is also an object of the present invention to provide a use of an 8-oxoprotoberberine derivative or a pharmaceutically acceptable salt thereof as a composition for preventing, improving, or treating diseases associated with the activity of NFAT5.

To achieve the above objects, the present invention provides the 8-oxoprotoberberine derivative represented by formula 1:

[Formula 1]

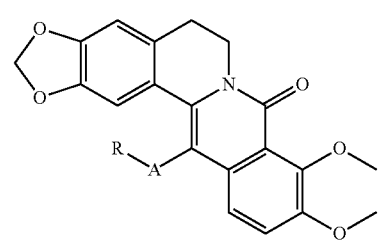

In the formula 1,
A is $C_{1-6}$ alkylene, —C(=O)—, or —NHC(=O)—;
R is hydroxyl, amino, straight or branched $C_{1-6}$ alkoxy, $C_{6-12}$ aryl, or 5~8 membered monocyclic or 8~11 membered bicyclic heteroaryl containing one or more hetero atoms selected from the group consisting of N, O, and S, wherein the aryl or heteroaryl is unsubstituted or substituted with one or more compounds selected from the group consisting of halogen, straight or branched $C_{1-6}$ alkyl, and $C_{1-6}$ alkoxy.

The present invention also provides a method for preparing the 8-oxoprotoberberine derivative represented by formula 1 comprising the following steps as shown in reaction formula 1:
preparing the compound represented by formula 4 via reaction between the compound represented by formula 2 and the compound represented by formula 3 (step 1); and
Preparing the compound represented by formula 1 by reacting the compound represented by formula 4 obtained in step 1) under basic condition (step 2):

[Reaction Formula 1]

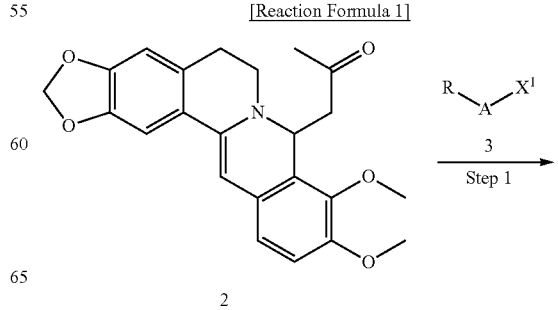

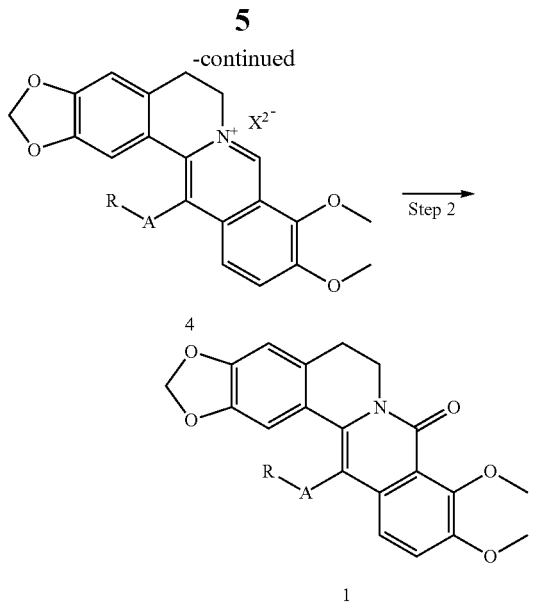

In the reaction formula 1, A and R are as defined above, and $X^1$ and $X^2$ are halogens.

The present invention further provides a pharmaceutical composition comprising an 8-oxoprotoberberine derivative or a pharmaceutically acceptable salt thereof as an active ingredient.

The present invention also provides a pharmaceutical composition for the prevention or treatment of diseases associated with the activity of NFAT5 comprising an 8-oxoprotoberberine derivative or a pharmaceutically acceptable salt thereof as an active ingredient.

The present invention also provides a NFAT5 activity inhibitor comprising an 8-oxoprotoberberine derivative or a pharmaceutically acceptable salt thereof as an active ingredient.

The present invention also provides a health functional food composition for the prevention or improvement of diseases associated with the activity of NFAT5 comprising an 8-oxoprotoberberine derivative or a pharmaceutically acceptable salt thereof as an active ingredient.

The present invention also provides a method for preventing, improving, or treating diseases associated with the activity of NFAT5 containing the step of administering an effective dose of an 8-oxoprotoberberine derivative or a pharmaceutically acceptable salt thereof to a subject.

In addition, the present invention provides a use of an 8-oxoprotoberberine derivative or a pharmaceutically acceptable salt thereof as a composition for preventing, improving, or treating diseases associated with the activity of NFAT5.

Advantageous Effect

The novel 8-oxoprotoberberine derivative or its pharmaceutically acceptable salt of the present invention displays a significantly increased oral absorption rate due to the improvement of physical properties, compared with the conventional protoberberine, suppresses the activity of NFAT5, inhibits the secretion of inflammatory cytokines, and reduces the expression of NFAT5 in rheumatoid arthritis mouse model, suggesting that the novel 8-oxoprotoberberine derivative or its pharmaceutically acceptable salt of the present invention can be useful as a pharmaceutical composition for the prevention or treatment of NFAT5 activity associated diseases, particularly rheumatoid arthritis or inflammatory diseases.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
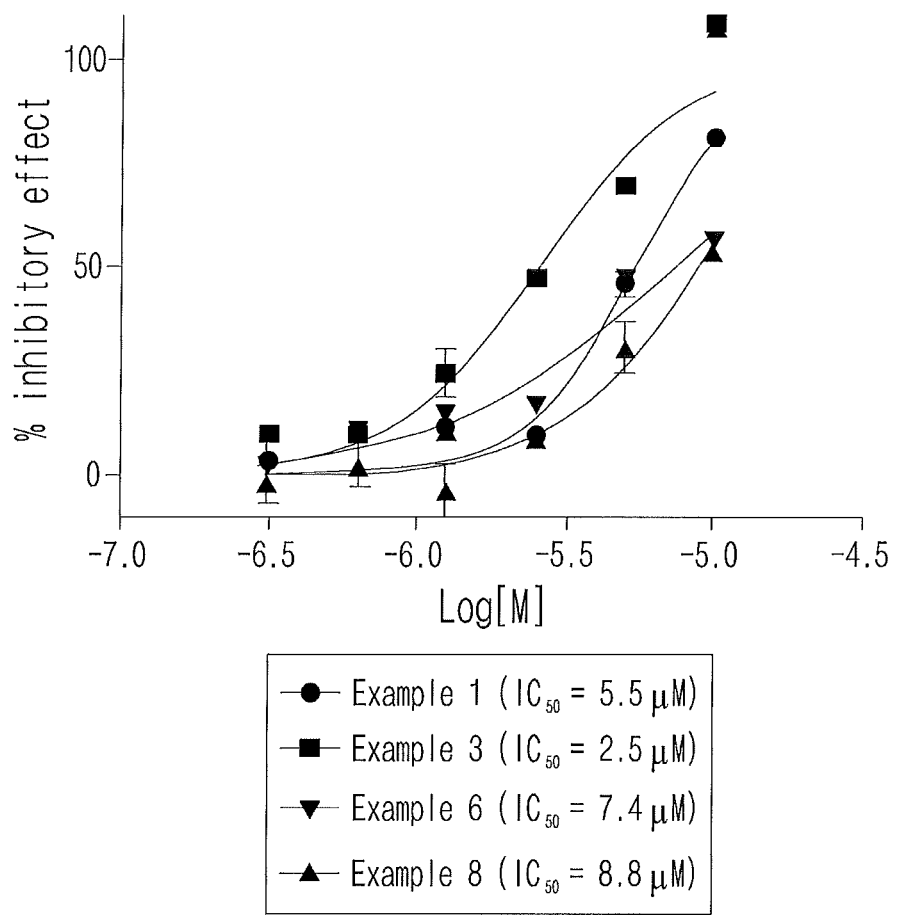
FIG. 1 is a graph illustrating the inhibitory effect of the derivative of the present invention on the transcription activity of NFAT5.

Hereinafter, the present invention is described in detail.

The present invention provides the 8-oxoprotoberberine derivative represented by formula 1 or a pharmaceutically acceptable salt thereof:

[Formula 1]

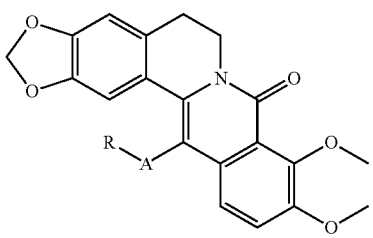 [SMILES: COc1ccc2c(C(=O)O)c3n(c(=O)c2c1OC)CCc1cc2c(cc1-3)OCO2]

In the formula 1,

A is $C_{1-6}$ alkylene, —C(=O)—, or —NHC(=O)—;

R is hydroxyl, amino, straight or branched $C_{1-6}$ alkoxy, $C_{6-12}$ aryl, or 5~8 membered monocyclic or 8~11 membered bicyclic heteroaryl containing one or more hetero atoms selected from the group consisting of N, O, and S, wherein the aryl or heteroaryl is unsubstituted or substituted with one or more compounds selected from the group consisting of halogen, straight or branched $C_{1-6}$ alkyl, and $C_{1-6}$ alkoxy.

A is preferably $C_{1-4}$ alkylene, —C(=O)—, or —NHC(=O)—, and more preferably $C_{1-2}$ alkylene, —C(=O)—, or —NHC(=O)—.

R is preferably hydroxyl, amino, straight or branched $C_{1-4}$ alkoxy, $C_{6-10}$ aryl, or 5~8 membered monocyclic or 8~11 membered bicyclic heteroaryl containing one or more hetero atoms selected from the group consisting of N, O, and S, wherein the aryl or heteroaryl is unsubstituted or substituted with one or more compounds selected from the group consisting of halogen, straight or branched $C_{1-6}$ alkyl, and $C_{1-6}$ alkoxy, and more preferably selected from the group consisting of hydroxyl, amino, straight or branched $C_{1-2}$ alkoxy, phenyl, pyridinyl, thiazolyl, and benzoimidazolyl, wherein the phenyl, pyridinyl, thiazolyl or benzoimidazolyl is unsubstituted or substituted with one or more compounds selected from the group consisting of halogen, straight or branched $C_{1-4}$ alkyl, and $C_{1-4}$ alkoxy.

When A is $C_{1-4}$ alkylene, R is selected from the group consisting of phenyl, pyridinyl, thiazolyl, and benzoimidazolyl unsubstituted or substituted with one or more compounds selected from the group consisting of halogen, methyl, and methoxy;

When A is —C(=O)—, R is hydroxyl, amino, straight or branched $C_{1-2}$ alkoxy, or phenyl unsubstituted or substituted with one or more halogens; and When A is —NHC(=O)—, R is phenyl unsubstituted or substituted with one or more halogens.

The 8-oxoprotoberberine derivative represented by formula 1 is more specifically exemplified by followings:

1) 13-(2-fluorobenzyl)-9,10-dimethoxy-5H-[1,3]dioxolo[4,5-g]isoquinolino[3,2-a]isoquinoline-8(6H)-one;

2) 13-(2,4-difluorobenzyl)-9,10-dimethoxy-5H-[1,3]dioxolo[4,5-g]isoquinolino[3,2-a]isoquinoline-8(6H)-one;

3) 13-(2,6-difluorobenzyl)-9,10-dimethoxy-5H-[1,3]dioxolo[4,5-g]isoquinolino[3,2-a]isoquinoline-8(6H)-one;

4) 9,10-dimethoxy-13-(2-methylbenzyl)-5,6-dihydro-[1,3]dioxolo[4,5-g]isoquinolino [3,2-a]isoquinoline-8(6H)-one;

5) 9,10-dimethoxy-13-(2-methoxybenzyl)-5,6-dihydro-[1,3]dioxolo[4,5-g]isoquinolino [3,2-a]isoquinoline-8(6H)-one;

6) 9,10-dimethoxy-13-(pyridine-2-ylmethyl)-5,6-dihydro-[1,3]dioxolo[4,5-g]isoquinolino [3,2-a]isoquinoline-8(6H)-one;

7) 13-((1H-benzo[d]imidazole-2-yl)methyl)-9,10-dimethoxy-5,6-dihydro-[1,3]dioxolo [4,5-g]isoquinolino[3,2-a]isoquinoline-8(6H)-one;

8) 13-((2-chlorothiazole-5-yl)methyl)-9,10-dimethoxy-5,6-dihydro-[1,3]dioxolo[4,5-g]isoquinolino[3,2-a]isoquinoline-8(6H)-one;

9) 13-(2-fluorobenzoyl)-9,10-dimethoxy-5H-[1,3]dioxolo[4,5-g]isoquinolino[3,2-a]isoquinoline-8(6H)-one;

10) 13-ethyl-9,10-dimethoxy-8-oxo-6,8-dihydro-5H-[1,3]dioxolo[4,5-g]isoquinolino[3,2-a]isoquinoline-13-carboxylate;

11) 9,10-dimethoxy-8-oxo-6,8-dihydro-5H-[1,3]dioxolo[4,5-g]isoquinolino[3,2-a]isoquinoline-13-carboxylic acid;

12) 9,10-dimethoxy-8-oxo-6,8-dihydro-5H-[1,3]dioxolo[4,5-g]isoquinolino[3,2-a]isoquinoline-13-carboxamide; and 13) N-(2-fluorophenyl)-9,10-dimethoxy-8-oxo-6,8-dihydro-5H-[1,3]dioxolo[4,5-g]isoquinolino[3,2-a]isoquinoline-13-carboxamide.

The preferable structure of the 8-oxoprotoberberine represented by formula 1 of the present invention is shown in Table 1.

TABLE 1

| Example | Structure |
|---------|-----------|
| 1 | 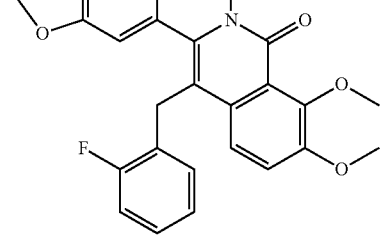 |
| 2 | 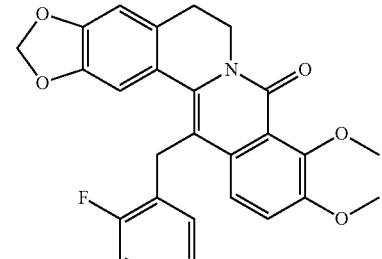 |
| 3 | 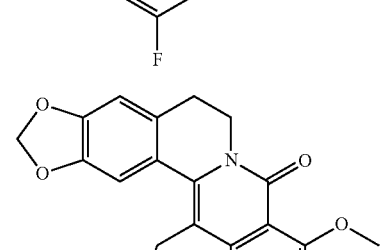 |

TABLE 1-continued

| Example | Structure |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |

The 8-oxoprotoberberine derivative represented by formula 1 of the present invention can be used as a form of a pharmaceutically acceptable salt, in which the salt is preferably acid addition salt formed by pharmaceutically acceptable free acids. The acid addition salt herein can be obtained from inorganic acids such as hydrochloric acid, nitric acid, phosphoric acid, sulfuric acid, hydrobromic acid, hydroiodic acid, nitrous acid, or phosphorous acid; non-toxic organic acids such as aliphatic mono/di-carboxylate, phenyl-substituted alkanoate, hydroxy alkanoate/alkanedioate, aromatic acids, aliphatic and aromatic sulfonic acids; or organic acids such as acetic acid, benzoic acid, citric acid, lactic acid, maleic acid, gluconic acid, methanesulfonic acid, 4-toluenesulfonic acid, tartaric acid, and fumaric acid. The pharmaceutically non-toxic salt is exemplified by sulfate, pyrosulfate, bisulfate, sulfite, bisulfite, nitrate, phosphate, monohydrogen phosphate, dihydrogen phosphate, metaphosphate, pyrophosphate chloride, bromide, iodide, fluoride, acetate, propionate, decanoate, caprylate, acrylate, formate, isobutylate, caprate, heptanoate, propiolate, oxalate, malonate, succinate, suberate, sebacate, fumarate, maliate, butin-1,4-dioate, hexane-1,6-dioate, benzoate, chlorobenzoate, methylbenzoate, dinitro benzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutylate, citrate, lactate, β-hydroxybutylate, glycolate, malate, tartrate, methanesulfonate, propanesulfonate, naphthalene-1-sulfonate, naphthalene-2-sulfonate, or mandelate.

The acid addition salt in this invention can be prepared by the conventional method known to those in the art. For example, the 8-oxoprotoberberine derivative represented by formula 1 of the present invention is dissolved in an organic solvent such as methanol, ethanol, acetone, dichloromethane, and acetonitrile, to which an organic acid or an inorganic acid is added. The obtained precipitate is filtered, and then dried to give an acid addition salt. Or the precipitate is vacuum-distillated with a solvent and excessive acid, followed by drying or crystallization in an organic solvent to give an acid addition salt.

A pharmaceutically acceptable metal salt can be prepared by using a base. Alkali metal or alkali earth metal salt is obtained by the following processes: dissolving the compound in excessive alkali metal hydroxide or alkali earth metal hydroxide solution; filtering non-soluble compound salt; evaporating the remaining solution and drying thereof. At this time, the metal salt is preferably prepared in the pharmaceutically suitable form of sodium, potassium, or calcium salt. And the corresponding silver salt is prepared by the reaction of alkali metal or alkali earth metal salt with a proper silver salt (ex; silver nitrate).

The present invention not only includes the 8-oxoprotoberberine derivative represented by formula 1 but also includes the pharmaceutically acceptable salts thereof, every possible solvates, and hydrates constructed from the same.

The novel 8-oxoprotoberberine derivative of the present invention is excellent in inhibiting the activity of NFAT5, particularly the derivatives of Examples 1, 3, 6, and 10 are remarkably excellent in inhibiting the activity of NFAT5 (see Experimental Examples 2 and 3). When the joint region of the test mouse was observed by the naked eye, the improvement of arthritis symptoms was confirmed. The significant improvement of arthritis symptoms was also confirmed by histological staining (see Experimental Example 10).

Therefore, the derivative of the present invention can be useful as a pharmaceutical composition for preventing or treating diseases associated with the activity of NFAT5.

The present invention also provides a method for preparing the 8-oxoprotoberberine derivative represented by formula 1 comprising the following steps as shown in reaction formula 1:

preparing the compound represented by formula 4 by reacting the compound represented by formula 2 with the compound represented by formula 3 (step 1); and preparing the compound represented by formula 1 by reacting the compound represented by formula 4 obtained in step 1) under basic condition (step 2):

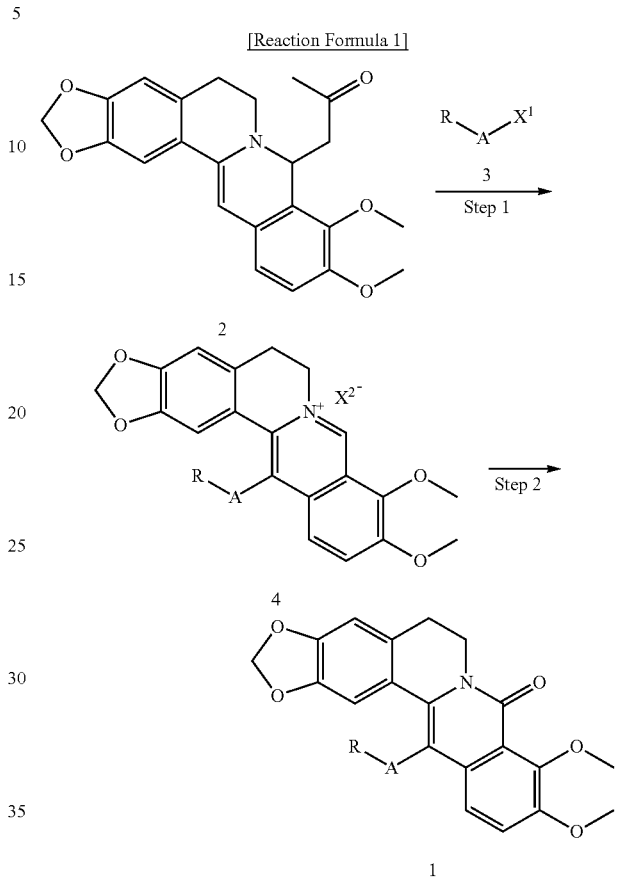

In the reaction formula 1, A and R are as defined above, and $X^1$ and $X^2$ are halogens.

Hereinafter, the said preparation method of the invention is described in more detail.

In the preparation method of the invention above, step 1) is to obtain the compound represented by formula 4 by reacting the compound represented by formula 2 with the compound represented by formula 3.

At this time, the compound represented by formula 3 is preferably mixed with the compound represented by formula 2 at the equivalent ratio of 1.2~2:1. To increase the reactivity, a catalyst such as sodium iodide, potassium iodide, sodium chloride, and potassium chloride can be used and at this time, sodium iodide is more preferred.

The solvent used in step 1) is preferably selected from the group consisting of acetonitrile, chloroform, dimethylformamide, dimethylsulfoxide, methanol, ethanol, propanol, butanol, tetrahydrofuran, dioxane, methylene chloride, 1,2-dimethoxyethane, and a mixture thereof, and more preferably acetonitrile is selected.

In the preparation method of the invention, step 2) is to obtain the compound represented by formula 1 by reacting the compound represented by formula 4 obtained in step 1) under basic condition.

At this time, the base can be any conventional base but potassium hydroxide, sodium hydroxide, calcium hydroxide, or strontium hydroxide is preferred and potassium hydroxide or sodium hydroxide solution is more preferred.

As shown in reaction formula 2, step 2) is composed of the following substeps:
preparing the compound represented by formula 5 via reduction reaction of the compound represented by formula 4 (step A); and
preparing the compound represented by formula 1 via oxidation reaction of the compound represented by formula 5 obtained in step A.:

[Reaction Formula 2]

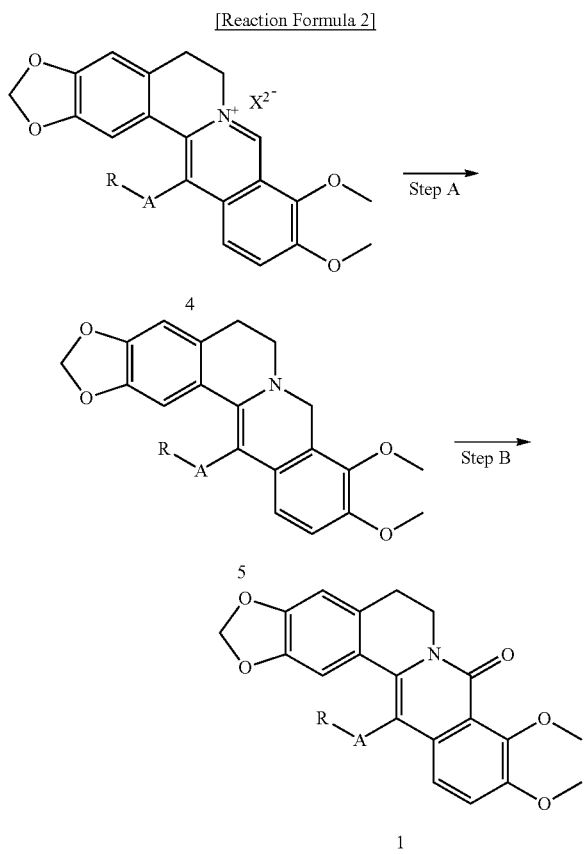

(In the reaction formula 2, A and R are as defined above, and $X^2$ is halogen).

Particularly, step A is to obtain the compound represented by formula 5 via reduction reaction of the compound represented by formula 4.

At this time, the reducing agent used herein is preferably selected from the group consisting of sodium borohydride, sodium cyanoborohydride, sodium triacetoxyborohydride, pyridine borochelating agent, and zinc borohydride, and sodium cyanoborohydride, sodium borohydride, or sodium triacetoxyborohydride is more preferred.

A base can be used as a catalyst, and at this time any conventional base can be used without limitation, but potassium hydroxide, sodium hydroxide, calcium hydroxide, or strontium hydroxide is preferred, and potassium hydroxide or sodium hydroxide solution is more preferred.

The solvent used herein is a single solvent selected or a mixture of those selected from the group consisting of alcohol solvents such as methanol, ethanol, propanol, and butanol; ether solvents such as tetrahydrofuran, dioxane, methylene chloride, and 1,2-dimethoxyethane; dimethylformamide; and dimethylsulfoxide.

Step B is to obtain the compound represented by formula 1 via oxidation reaction of the compound represented by formula 5 obtained in step A.

At this time, the oxidizing agent used herein is preferably selected from the group consisting of manganese dioxide, hydrogen peroxide, and potassium dichromate, and manganese dioxide is more preferred.

The solvent used herein is preferably selected from the group consisting of ether solvents such as methylene chloride and 1,2-dimethoxyethane; dimethylformamide; and dimethylsulfoxide.

After the reaction, extraction using an organic solvent, drying, filtration, and distillation under reduced pressure follow, and additionally column chromatography or recrystallization can be performed.

The present invention also provides a pharmaceutical composition for the prevention or treatment of diseases associated with the activity of NFAT5 comprising the novel 8-oxoprotoberberine derivative or the pharmaceutically acceptable salt thereof as an active ingredient.

Herein, the disease associated with the activity of NFAT5 is arthritis or auto-immune disease.

The arthritis herein is characteristically rheumatoid arthritis.

The auto-immune disease herein is one or more diseases selected from the group consisting of systemic scleroderma, lupus erythematosus, atopic dermatitis, Behcet's disease, Sjogren's syndrome, multiple sclerosis, and Graves' hyperthyroidism.

In a preferred embodiment of the present invention, the novel 8-oxoprotoberberine derivative demonstrated excellence in inhibiting NFAT5 activity. Particularly, the derivatives of Examples 1, 3, 6, and 10 were remarkably excellent in inhibiting NFAT5 activity (see Experimental Examples 2 and 3). When the joint region of the test mouse was observed by the naked eye, the improvement of arthritis symptoms was confirmed. The significant improvement of arthritis symptoms was also confirmed by histological staining (see Experimental Example 11). The compound of the present invention inhibited the up-regulation of iNOS induced by LPS (see Table 2), inhibited the transcriptional activity of NFAT5 (see Table 3 and FIG. 1), and suppressed other transcription factors such as NF-kB, NFATc, CREB, and ELK (see FIG. 2). However, the compound of the present invention neither inhibits the inducement of ROS and the activity of p38 nor inhibits COX1 and COX2 (see FIGS. 3 and 6, and Tables 4 and 5). The compound of the present invention did not display cytotoxicity but inhibited the secretion of inflammatory cytokines (see Table 6 and FIG. 6). In the mouse model having rheumatoid arthritis induced by collagen, the compound of the present invention improved arthritis symptoms (see FIG. 7) and reduced the expression of inflammatory cytokines (TNF-α, IL-6) (see FIG. 8). In addition, the compound of the present invention was confirmed to have the increased oral absorption (see Table 7); to inhibit the secretion of inflammatory cytokines in human mononuclear cells (see FIG. 11); and to inhibit the differentiation of T cells into Th17 cells (see FIG. 12).

As confirmed hereinbefore, the novel 8-oxoprotoberberine derivative or its pharmaceutically acceptable salt of the present invention demonstrates significantly increased oral absorption rate due to the improvement of physical properties, compared with the conventional protoberberine, and has the ability to directly inhibit NFAT5 transcription without using NFAT5 upstream p38 pathway, resulting in the inhibition of the activity of NFAT5 and the secretion of inflammatory cytokines. Therefore, the novel derivative or its pharmaceutically acceptable salt of the present invention can be used as a pharmaceutical composition for the prevention or treatment of NFAT5 activity associated disease, particularly rheumatoid arthritis, by inhibiting the expression of NFAT5, confirmed in the test mouse with rheumatoid arthritis.

The 8-oxoprotoberberine derivative represented by formula 1 or the pharmaceutically acceptable salt thereof of the present invention can be prepared for oral or parenteral administration by mixing with generally used diluents or excipients such as fillers, extenders, binders, wetting agents, disintegrating agents and surfactant.

Solid formulations for oral administration are tablets, pills, powders, granules and capsules. These solid formulations are prepared by mixing the 8-oxoprotoberberine derivative represented by formula 1 or the pharmaceutically acceptable salt thereof of the present invention with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin.

Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerol, gelatin, etc.

The effective dosage of the 8-oxoprotoberberine derivative represented by formula 1 or the pharmaceutically acceptable salt thereof of the present invention can be adjusted according to age, weight, and gender of patient, administration pathway, health condition, and severity of disease, etc. The effective dosage for an adult in the weight of 70 Kg is preferably 0.1~1,000 mg/day, and more preferably 1~500 mg/day, which can be administered orally or parenterally several times a day or preferably once a day or a couple of times a day according to the judgment of a doctor or a pharmacist.

The pharmaceutical composition of the present invention can be administered alone or together with surgical operation, hormone therapy, chemo-therapy and biological regulators for the prevention or treatment of arthritis or auto-immune disease.

The present invention also provides a health functional food composition for the prevention or improvement of diseases associated with the activity of NFAT5 comprising the novel 8-oxoprotoberberine derivative or the pharmaceutically acceptable salt thereof as an active ingredient.

Since the derivative of the present invention is excellent in inhibiting NFAT5 activity, it can be useful as a health functional food composition for the prevention or improvement of diseases associated with the activity of NFAT5.

Herein, the disease associated with the activity of NFAT5 is arthritis or auto-immune disease.

The arthritis herein is characteristically rheumatoid arthritis.

The auto-immune disease herein is one or more diseases selected from the group consisting of systemic scleroderma, lupus erythematosus, atopic dermatitis, Behcet's disease, Sjogren's syndrome, multiple sclerosis, and Graves' hyperthyroidism.

The novel 8-oxoprotoberberine derivative or its pharmaceutically acceptable salt of the present invention demonstrates significantly increased oral absorption rate due to the improvement of physical properties, compared with the conventional protoberberine, and has the ability to directly inhibit NFAT5 transcription without using NFAT5 upstream p38 pathway, resulting in the inhibition of the activity of NFAT5 and the secretion of inflammatory cytokines. Therefore, the novel derivative or its pharmaceutically acceptable salt of the present invention can be used as a health functional food composition for the prevention or improvement of diseases associated with the activity of NFAT5, particularly rheumatoid arthritis, by inhibiting the expression of NFAT5, confirmed in the test mouse with rheumatoid arthritis.

The food herein is not limited. For example, the compound of the invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The 8-oxoprotoberberine derivative represented by formula 1 of the present invention can be used as a food additive. In that case, the 8-oxoprotoberberine derivative represented by formula 1 of the present invention can be added as it is or as mixed with other food components according to the conventional method. The mixing ratio of active ingredients can be regulated according to the purpose of use (prevention or improvement). In general, to produce health food or beverages, the 8-oxoprotoberberine derivative represented by formula 1 of the present invention is added preferably by 0.1~90 weight part. However, if long term administration is required for health and hygiene or regulating health condition, the content can be lower than the above but higher content can be accepted as well since the compound has been proved to be very safe.

The composition for health beverages of the present invention can additionally include various flavors or natural carbohydrates, etc, like other beverages in addition to the compound of the invention. The natural carbohydrates above can be one of monosaccharides such as glucose and fructose; disaccharides such as maltose and sucrose; polysaccharides such as dextrin and cyclodextrin; and sugar alcohols such as xylitol, sorbitol and erythritol. Besides, natural sweetening agents (thaumatin, stevia extract, for example rebaudioside A, glycyrrhizin, etc.) and synthetic sweetening agents (saccharin, aspartame, etc.) can be included as a sweetening agent. The content of the natural carbohydrate is preferably 1~20 g and more preferably 5~12 g in 100 g of the composition of the present invention.

In addition to the ingredients mentioned above, the 8-oxoprotoberberine derivative represented by formula 1 of the present invention can include in variety of nutrients, vitamins, minerals (electrolytes), flavors including natural flavors and synthetic flavors, coloring agents and extenders (cheese, chocolate, etc.), pectic acid and its salts, alginic acid and its salts, organic acid, protective colloidal viscosifiers, pH regulators, stabilizers, antiseptics, glycerin, alcohols, carbonators which used to be added to soda, etc. The 8-oxoprotoberberine derivative of the present invention can also include natural fruit juice, fruit beverages and/or fruit flesh addable to vegetable beverages.

The present invention also provides a method for preventing, improving, or treating diseases associated with the activity of NFAT5 containing the step of administering an effective dose of the 8-oxoprotoberberine derivative or the pharmaceutically acceptable salt thereof to a subject.

Further, the present invention provides a use of the 8-oxoprotoberberine derivative or the pharmaceutically acceptable salt thereof as a preventive or therapeutic agent for diseases associated with the activity of NFAT5.

In addition, the present invention provides a use of the 8-oxoprotoberberine derivative or the pharmaceutically acceptable salt thereof as a health functional food composition for the prevention or improvement of diseases associated with the activity of NFAT5.

The derivative of the present invention, therefore, can be used as a preventive or therapeutic agent for the prevention or treatment of diseases associated with the activity of NFAT5 and as a health functional food composition for the improvement of the disease.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1: 8-acetonyldihydroberberine

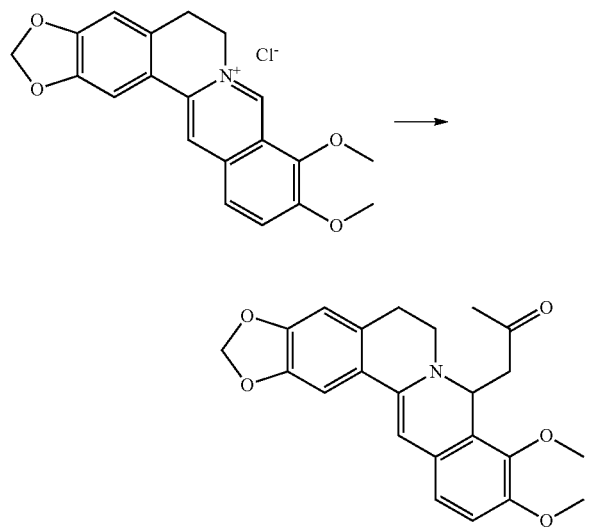 [SMILES: COc1ccc2cc3[n+](cc2c1OC)CCc1cc2c(cc1-3)OCO2 ; [Cl-] ; COc1ccc2c(c1OC)C(CC(C)=O)N1CCc3cc4c(cc3C1=C2)OCO4]

Hydrochloride berberine (5 g, 13.45 mmol) was added to 5 N sodium hydroxide aqueous solution (23 mL), which was cooled down at 0° C. Acetone (5 mL, 67.23 mmol) was slowly added thereto. After stirring the mixture at room temperature for 1 hour, the generated solid was filtered, followed by washing twice with 40 mL of 80% methanol. The filtrate was dried and as a result the target compound (4.65 g, 89%) was obtained.

$^1$H NMR (300 MHz, CDCl$_3$) δ 2.04 (s, 3H), 2.37-2.44 (dd, J=3.0, 15.0 Hz, 1H), 2.76-2.84 (m, 2H), 3.08-3.11 (dd, J=6.0, 15.0 Hz, 1H), 3.30-3.36 (m, 2H), 3.83 (s, 3H), 3.89 (s, 3H), 5.30-5.34 (dd, J=3.0, 6.0 Hz, 1H), 5.89 (s, 1H), 5.93-5.94 (d, J=3.0 Hz, 1H), 6.57 (s, 1H), 6.76-6.79 (m, 2H), 7.13 (s, 1H).

Example 1: 13-(2-fluorobenzyl)-9,10-dimethoxy-5H-[1,3]dioxolo[4,5-g]isoquinolino[3,2-a]isoquinoline-8(6H)-one

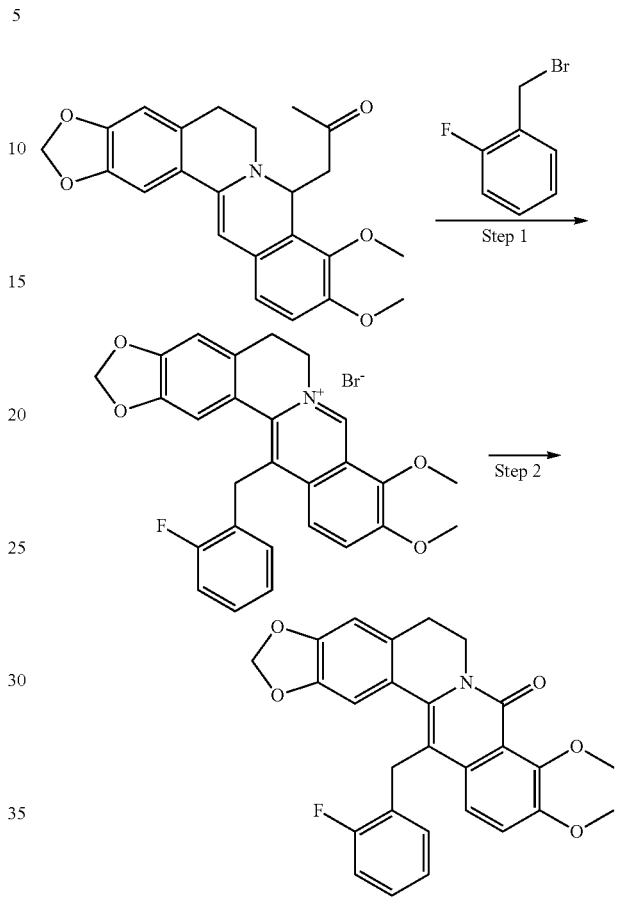

Step 1: 13-(2-fluorobenzyl)-9,10-dimethoxy-5H-[1,3]dioxolo[4,5-g]isoquinolino[3,2-a]isoquinoline-7-iumbromide The 8-acetonyldihydroberberine (1 g) obtained in Preparative Example 1 was dissolved in acetonitrile (20 mL), to which 2-fluorobenzylbromide (2 equivalent) and sodium iodide (0.54 g, 3.55 mmol, 1.2 equivalent) were added, followed by stirring at 80° C. for 4 hours. Upon completion of the reaction, the reactant was filtered and washed with methylene chloride (3×20 mL). The organic layer was washed with distilled water (5 mL), dried over sodium sulfate, and concentrated. The residue was separated by flash column chromatography (methylene chloride:methanol=20:1~10:1) to give the target compound as a yellow solid (45%).

$^1$H NMR (300 MHz, CDCl$_3$) δ 3.27-3.31 (t, J=6.0 Hz, 2H), 4.02 (s, 3H), 4.43 (s, 3H), 4.63 (s, 2H), 5.21 (s, 2H), 6.02 (s, 2H), 6.76-6.81 (m, 1H), 6.88-6.89 (m, 2H), 7.02-7.07 (m, 1H), 7.19-7.25 (m, 1H), 7.29-7.34 (m, 1H), 7.54-7.57 (d, J=9.0 Hz, 1H), 7.69-772 (d, J=9.0 Hz, 1H), 10.49 (s, 1H).

Step 2: 13-(2-fluorobenzyl)-9,10-dimethoxy-5H-[1,3]dioxolo[4,5-g]isoquinolino[3,2-a]isoquinoline-8(6H)-one The 13-(2-fluorobenzyl)-9,10-dimethoxy-5H-[1,3]dioxolo[4,5-g]isoquinolino[3,2-a]isoquinoline-7-iumbromide obtained in step 1) was dispersed in 50% tetrahydrofuran, to which potassium ferricyanide (10 equivalent) dissolved in 10% potassium hydroxide was added at 8~10° C., followed by stirring for 30 minutes. The mixture was stirred again at room temperature for 10 hours. The reactant was extracted with dichloromethane, dried over sodium sulfate, filtered, and then concentrated under reduced pressure. The residue was separated by flash column chromatography to give the target compound (28%).

$^1$H NMR (300 MHz, CDCl$_3$) δ 2.82-2.86 (t, J=6.0 Hz, 2H), 3.89 (s, 3H), 4.03 (s, 3H), 4.31 (s, 2H), 5.92 (s, 2H), 6.75 (s, 1H), 6.78 (s, 1H), 6.92-7.03 (m, 2H), 7.11-7.27 (m, 4H).

Example 1: 13-(2,4-difluorobenzyl)-9,10-dimethoxy-5H-[1,3]dioxolo[4,5-g]isoquinolino[3,2-a]isoquinoline-8(6H)-one

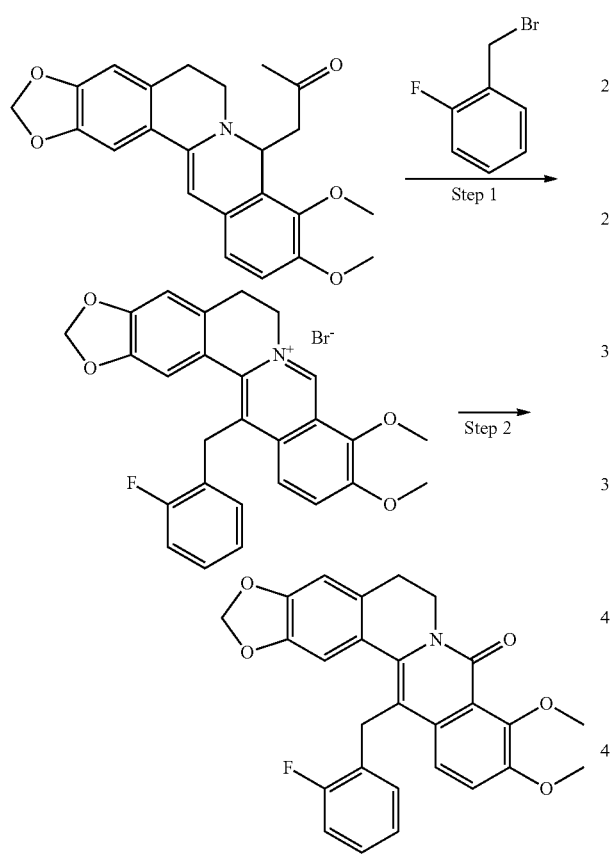

Step 1: 13-(2,4-difluorobenzyl)-9,10-dimethoxy-5H-[1,3]dioxolo[4,5-g]isoquinolino[3,2-a]isoquinoline-7-iumbromide A target compound (55%) was obtained by the same manner as described in step 1) of Example 1 except that 2,4-difluorobenzyl bromide was used instead of 2-fluorobenzyl bromide in step 1) of Example 1.

$^1$H NMR (300 MHz, CDCl$_3$) δ 3.27 (s, 2H), 4.03 (s, 3H), 4.42 (s, 3H), 4.58 (s, 2H), 5.28 (s, 2H), 6.03 (s, 2H), 6.72-6.82 (m, 3H), 6.89 (s, 1H), 6.96-7.02 (m, 1H), 7.50-7.53 (d, J=9.0 Hz, 1H), 7.70-77 (d, J=9.0 Hz, 1H), 10.68 (s, 1H).

Step 2: 13-(2,4-difluorobenzyl)-9,10-dimethoxy-5H-[1,3]dioxolo[4,5-g]isoquinolino[3,2-a]isoquinoline-8(6H)-one A target compound (25%) was obtained by the same manner as described in step 2) of Example 1 except that the 13-(2,4-difluorobenzyl)- 9,10-dimethoxy-5H-[1,3]dioxolo[4,5-g]isoquinolino[3,2-a]isoquinoline-7-iumbromide obtained in step 1) of Example 2 was used instead of 13-(2-fluorobenzyl)-9,10-dimethoxy-5H-[1,3]dioxolo[4,5-g]isoquinolino[3,2-a]isoquinoline-7-iumbromide in step 2) of Example 1.

$^1$H NMR (300 MHz, CDCl$_3$) δ 2.84 (s, 2H), 3.91 (s, 3H), 4.03 (s, 3H), 4.25 (s, 2H), 5.94 (s, 2H), 6.73-6.76 (m, 3H), 6.86-6.91 (m, 2H), 7.09-7.12 (d, J=9.0, 1H), 7.20-7.23 (d, J=9.0,1H).

Example 3: 13-(2,6-difluorobenzyl)-9,10-dimethoxy-5H-[1,3]dioxolo[4,5-g]isoquinolino[3,2-a]isoquinoline-8(6H)-one

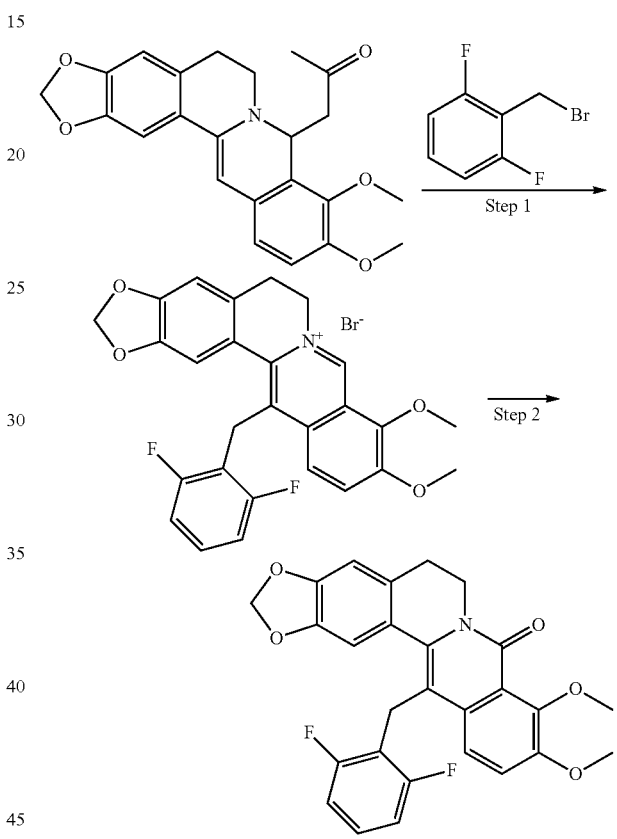

Step 1: 13-(2,6-difluorobenzyl)-9,10-dimethoxy-5H-[1,3]dioxolo[4,5-g]isoquinolino[3,2-a]isoquinoline-7-iumbromide A target compound (27%) was obtained by the same manner as described in step 1) of Example 1 except that 2,6-difluorobenzyl bromide was used instead of 2-fluorobenzyl bromide in step 1) of Example 1.

$^1$H NMR (300 MHz, CDCl$_3$) δ 3.24-3.28 (t, J=6.0 Hz, 2H), 4.02 (s, 3H), 4.37 (s, 3H), 4.74 (s, 2H), 5.21 (s, 2H), 6.07 (s, 2H), 6.83-6.88 (m, 2H), 6.93 (s, 1H), 7.05 (s, 1H), 7.17-7.25 (m, 1H), 7.73 (s, 2H), 10.45 (s, 1H).

Step 2: 13-(2,6-difluorobenzyl)-9,10-dimethoxy-5H-[1,3]dioxolo[4,5-g]isoquinolino[3,2-a]isoquinoline-8(6H)-one A target compound (26%) was obtained by the same manner as described in step 2) of Example 1 except that the 13-(2,6-difluorobenzyl)-9,10-dimethoxy-5H-[1,3]dioxolo[4,5-g]isoquinolino[3,2-a]isoquinoline-7-iumbromide obtained in step 1) of Example 3 was used instead of 13-(2-fluorobenzyl)-9,10-dimethoxy-5H-[1,3]dioxolo[4,5-g]isoquinolino[3,2-a]isoquinoline-7-iumbromide in step 2) of Example 1.

¹H NMR (300 MHz, CDCl₃) δ=2.85(s,2H),3.89 (s, 3H), 3.99 (s, 3H), 4.22 (s, 2H), 4.42 (s, 2H), 6.75-6.79 (m, 3H), 6.96 (s, 1H), 7.08-7.13 (m, 1H), 7.21-7.24 (d, J=9.0,1H), 7.35-7.38 (d, J=9.0,1H)

Example 4: 9,10-dimethoxy-13-(2-methylbenzyl)-5,6-dihydro-[1,3]dioxolo[4,5-g]isoquinolino [3,2-a]isoquinoline-8(6H)-one

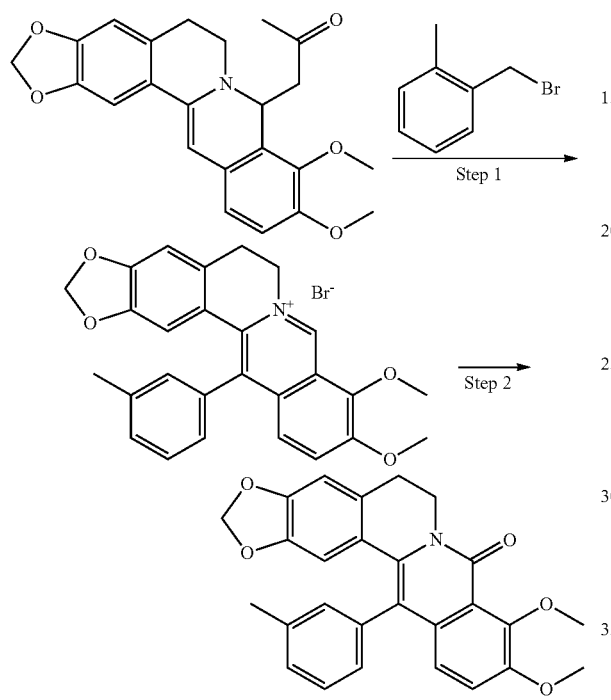

Step 1: 9,10-dimethoxy-13-(2-methylbenzyl)-5,6-dihydro-[1,3]dioxolo[4,5-g]isoquinolino [3,2-a]isoquinoline-7-iumbromide A target compound (28%) was obtained by the same manner as described in step 1) of Example 1 except that 2-methylbenzyl bromide was used instead of 2-fluorobenzyl bromide in step 1) of Example 1.

¹H NMR (300 MHz, CDCl₃) δ 2.46 (s, 3H), 3.29-3.33 (t, J=6.0 Hz, 2H),4.02 (s, 3H), 4.42 (s, 3H), 4.46 (s, 2H), 5.19 (s, 2H), 5.99 (s, 2H), 6.63-6.66 (d, J 9.0 Hz, 1H), 6.83-6.87 (m, 2H), 7.07-7.10 (d, J=9.0 Hz, 1H), 7.22-7.27 (m, 1H), 7.36-7.38 (m, 1H), 7.51-7.54 (m, 1H), 7.68-7.71 (m, 1H), 10.44 (s, 1H).

Step 2: 9,10-dimethoxy-13-(2-methylbenzyl)-5,6-dihydro-[1,3]dioxolo[4,5-g]isoquinolino [3,2-a]isoquinoline-8(6H)-one The 9,10-dimethoxy-13-(2-methylbenzyl)-5,6-dihydro-[1,3]dioxolo[4,5-g]isoquinolino [3,2-a]isoquinoline-7-iumbromide obtained in step 1) was added to 20% potassium hydroxide solution, followed by reflux for 24 hours. Upon completion of the reaction, the reactant was extracted with dichloromethane, dried over sodium sulfate, filtered, and concentrated under reduced pressure. The residue was separated by flash column chromatography to give the target compound (12%).

¹H NMR (300 MHz, CDCl₃) δ 2.40 (s, 3H), 2.81-2.85 (t, J=6.0 Hz, 2H), 3.89 (s, 3H), 4.04 (s, 3H), 4.15 (s, 2H), 5.89 (s, 2H), 6.73 (s, 1H), 6.76 (s, 1H), 6.90-6.92 (d, J=6.0 Hz, 1H),7.04-7.20(m,4H),7.26-7.30(m,1H).

Example 5: 9,10-dimethoxy-13-(2-methoxybenzyl)-5,6-dihydro-[1,3]dioxolo[4,5-g]isoquinolino [3,2-a]isoquinoline-8(6H)-one

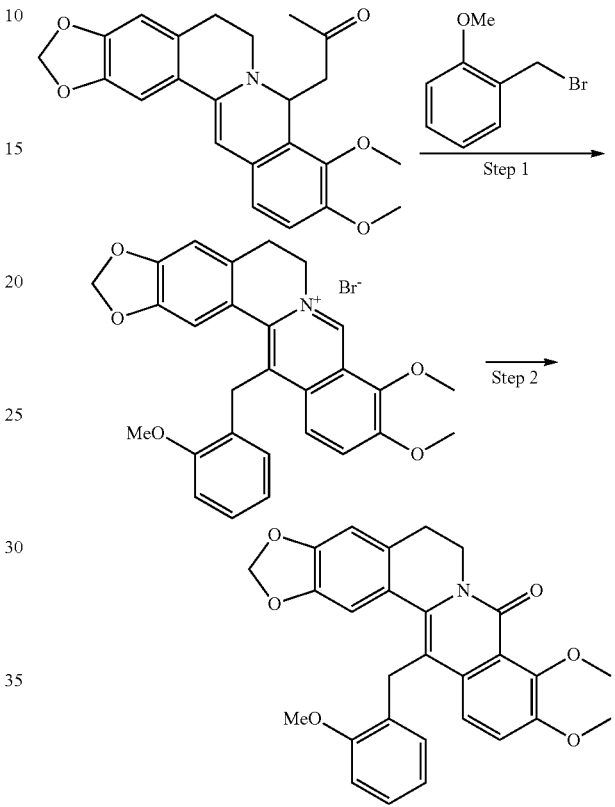

Step 1: 9,10-dimethoxy-13-(2-methoxybenzyl)-5,6-dihydro-[1,3]dioxolo[4,5-g]isoquinolino [3,2-a]isoquinoline-7-iumbromide A target compound (89%) was obtained by the same manner as described in step 1) of Example 1 except that 2-methoxybenzyl bromide was used instead of 2-fluorobenzyl bromide in step 1) of Example 1.

¹H NMR (300 MHz, CDCl₃) δ 3.26-3.30 (t, J=6.0 Hz, 2H),3.96 (s, 3H), 4.02 (s, 3H), 4.41 (s, 3H), 4.52 (s, 2H), 5.22 (s, 2H), 5.99 (s, 2H), 6.63-6.68 (m, 2H), 6.78-6.92 (m, 3H), 7.01-7.04 (m, 1H), 7.56-7.71 (m, 2H), 10.43 (s, 1H).

Step 2: 9,10-dimethoxy-13-(2-methoxybenzyl)-5,6-dihydro-[1,3]dioxolo[4,5-g]isoquinolino [3,2-a]isoquinoline-8(6H)-one A target compound (14%) was obtained by the same manner as described in step 2) of Example 4 except that the 9,10-dimethoxy-13-(2-methoxybenzyl)-5,6-dihydro-[1,3]dioxolo[4,5-g]isoquinolino[3,2-a]isoquinoline-7-iumbromide obtained in step 1) was used instead of 9,10-dimethoxy-13-(2-methylbenzyl)-5,6-dihydro-[1,3]dioxolo[4,5-g]isoquinolino [3,2-a]isoquinoline-7-iumbromide in Example 4.

¹H NMR (300 MHz, CDCl₃) δ 2.81-2.85 (t, J=6.0 Hz, 2H),3.89 (s, 3H), 3.96 (s, 3H), 4.03 (s, 3H), 4.21 (s, 2H), 5.90 (s, 2H), 6.73 (s, 1H), 6.79-6.89 (m, 3H), 6.95-6.98 (d, J=9.0 Hz, 1H),7.17-7.3 (m, 3H).

Example 6: 9,10-dimethoxy-13-(pyridine-2-ylmethyl)-5,6-dihydro-[1,3]dioxolo[4,5-g]isoquinolino[3,2-a]isoquinoline-8(6H)-one

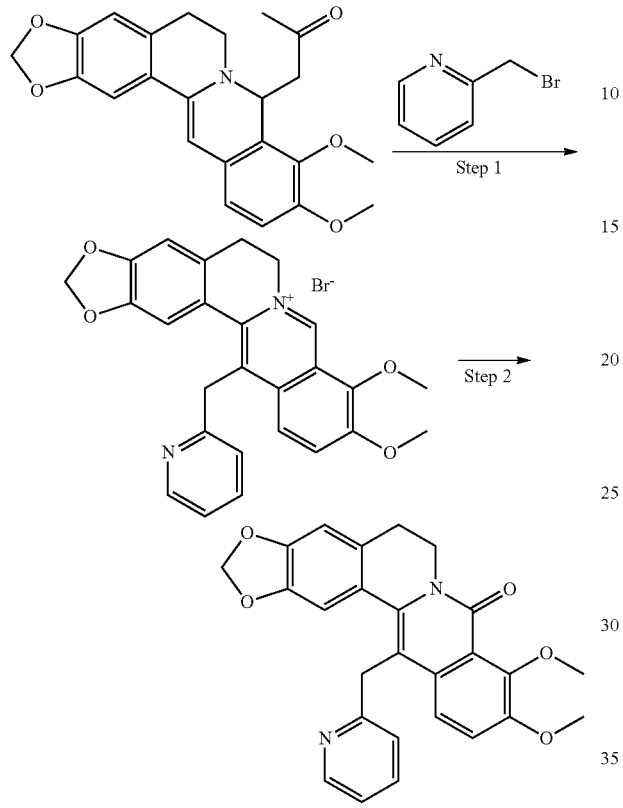

Step 1: 9,10-dimethoxy-13-(pyridine-2-ylmethyl)-5,6-dihydro-[1,3]dioxolo[4,5-g]isoquinolino [3,2-a]isoquinoline-7-iumbromide A target compound (7%) was obtained by the same manner as described in step 1) of Example 1 except that 2-cyanobenzyl bromide was used instead of 2-fluorobenzyl bromide in step 1) of Example 1.

$^1$H NMR (300 MHz, CDCl$_3$) δ 3.27 (s, 1H), 3.99 (s, 3H), 4.30 (s, 3H), 4.86 (s, 2H), 5.24 (s, 2H), 6.01 (s, 2H), 6.89 (s, 1H), 7.23-7.31 (m, 1H), 7.36 (s, 1H), 7.48-7.50 (m, 1H), 7.58-7.61 (d, J=9.0 Hz, 1H), 7.71-7.74 (d, J=9.0 Hz, 1H), 7.77-7.82 (m, 1H), 8.48-8.49 (d, J=3.0 Hz, 1H), 10.47 (s, 1H).

Step 2: 9,10-dimethoxy-13-(pyridine-2-ylmethyl)-5,6-dihydro-[1,3]dioxolo[4,5-g]isoquinolino [3,2-a]isoquinoline-8(6H)-one A target compound (15%) was obtained by the same manner as described in step 2) of Example 4 except that the 9,10-dimethoxy-13-(pyridine-2-ylmethyl)-5,6-dihydro-[1,3]dioxolo[4,5-g]isoquinolino [3,2-a]isoquinoline-7-iumbromide obtained in step 1) was used instead of 9,10-dimethoxy-13-(2-methylbenzyl)-5,6-dihydro-[1,3]dioxolo[4,5-g]isoquinolino [3,2-a]isoquinoline-7-iumbromide in Example 4.

$^1$H NMR (300 MHz, CDCl$_3$) δ 2.83-2.87 (t, J=6.0 Hz, 2H), 3.89 (s, 3H), 4.01 (s, 3H), 4.53 (s, 2H), 5.92 (s, 2H), 6.76 (s, 1H), 7.00 (s, 1H), 7.11-7.20 (m, 4H), 7.59-7.64 (m, 1H), 8.63-8.65 (d, J=6.0 Hz, 1H).

Example 7: 13-((1H-benzo[d]imidazole-2-yl)methyl)-9,10-dimethoxy-5,6-dihydro-[1,3]dioxolo[4,5-g]isoquinolino[3,2-a]isoquinoline-8(6H)-one

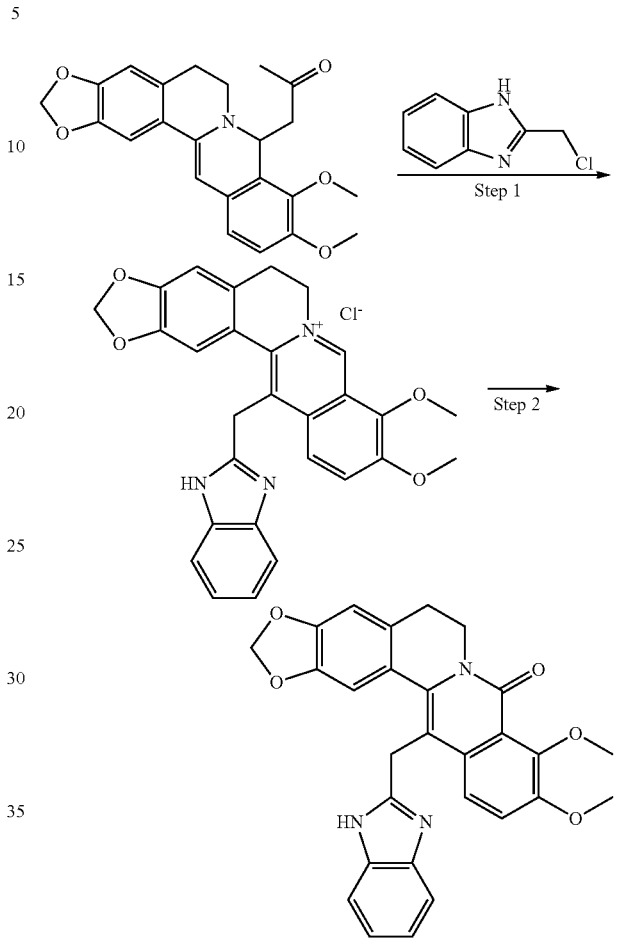

Step 1: 13-((1H-benzo[d]imidazole-2-yl)methyl)-9,10-dimethoxy-5,6-dihydro-[1,3]dioxolo [4,5-g]isoquinolino[3,2-a]isoquinoline-7-iumbromide A target compound (59%) was obtained by the same manner as described in step 1) of Example 1 except that 2-chloromethylbenzoimidazole was used instead of 2-fluorobenzyl bromide in step 1) of Example 1.

$^1$H NMR (300 MHz, CDCl$_3$) δ 3.31 (s, 2H), 3.80 (s, 3H), 4.14 (s, 3H), 4.87 (s, 2H), 5.11 (s, 2H), 5.99 (s, 2H), 6.83 (s, 1H), 7.16-7.19 (m, 2H), 7.46-7.49 (d, J=9.0 Hz, 1H), 7.60-7.63 (m, 2H), 7.72 (s, 1H), 7.80-7.83 (d, J=9.0 Hz, 1H), 9.83 (s, 1H).

Step 2: 13-((1H-benzo[d]imidazole-2-yl)methyl)-9,10-dimethoxy-5,6-dihydro-[1,3]dioxolo [4,5-g]isoquinolino[3,2-a]isoquinoline-8(6H)-one A target compound (8%) was obtained by the same manner as described in step 2) of Example 4 except that the 13-((1H-benzo[d]imidazole-2-yl)methyl)-9,10-dimethoxy-5,6-dihydro-[1,3]dioxolo [4,5-g]isoquinolino[3,2-a]isoquinoline-7-iumbromide obtained in step 1) was used instead of 9,10-dimethoxy-13-(2-methylbenzyl)-5,6-dihydro-[1,3]dioxolo[4,5-g]isoquinolino [3,2-a]isoquinoline-7-iumbromide in Example 4.

$^1$H NMR (300 MHz, CDCl$_3$) δ 2.81-2.85 (t, J=6.0 Hz, 2H), 3.81 (s, 3H), 3.85 (s, 3H), 3.98 (s, 3H), 4.22-4.24 (m,

2H), 4.45 (s, 2H), 5.90 (s, 2H), 6.77 (s, 1H), 7.09-7.38 (m, 6H), 7.72-7.74 (d, J=6.0 Hz, 1H).

Example 8: 13-((2-chlorothiazole-5-yl)methyl)-9,10-dimethoxy-5,6-dihydro-[1,3]dioxolo[4,5-g]isoquinolino[3,2-a]isoquinoline-8(6H)-one

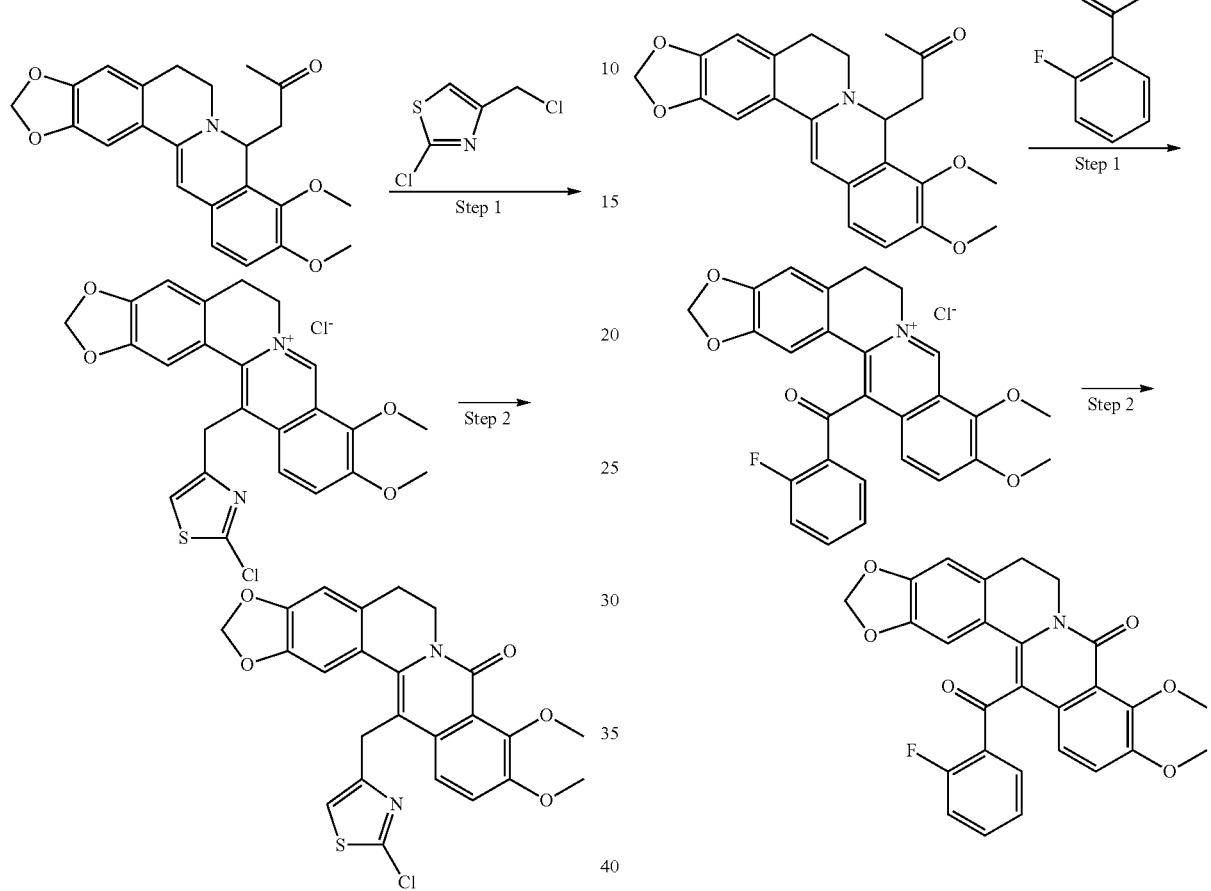

Step 1: 13-((2-chlorothiazole-5-yl)methyl)-9,10-dimethoxy-5,6-dihydro-[1,3]dioxolo[4,5-g]isoquinolino[3,2-a]isoquinoline-7-iumbromide A target compound (51%) was obtained by the same manner as described in step 1) of Example 1 except that 2-chloro-5-chloromethylthiazole was used instead of 2-fluorobenzyl bromide in step 1) of Example 1.

$^1$H NMR (300 MHz, CDCl$_3$) δ 3.31 (s, 1H), 4.06 (s, 3H), 4.40 (s, 3H), 4.71 (s, 2H), 5.12 (s, 2H), 6.07 (s, 2H), 6.91 (s, 1H), 6.98 (s, 1H), 7.09 (s, 1H), 7.71-7.75 (d, J=9.0 Hz, 1H), 7.80-7.83 (d, J=9.0 Hz, 1H), 10.39 (s, 1H).

Step 2: 13-((2-chlorothiazole-5-yl)methyl)-9,10-dimethoxy-5,6-dihydro-[1,3]dioxolo[4,5-g]isoquinolino[3,2-a]isoquinoline-8(6H)-one A target compound (5%) was obtained by the same manner as described in step 2) of Example 4 except that the 13-((2-chlorothiazole-5-yl)methyl)-9,10-dimethoxy-5,6-dihydro-[1,3]dioxolo[4,5-g]isoquinolino[3,2-a]isoquinoline-7-iumbromide obtained in step 1) was used instead of 9,10-dimethoxy-13-(2-methylbenzyl)-5,6-dihydro-[1,3]dioxolo[4,5-g]isoquinolino[3,2-a]isoquinoline-7-iumbromide in Example 4.

$^1$H NMR (300 MHz, CDCl$_3$) δ 2.87-2.91 (t, J=6.0, 2H), 3.95 (s, 3H), 4.01 (s, 3H), 4.27-4.31 (t, J=6.0 Hz, 2H), 6.01 (s, 2H), 6.70-6.72 (m, 2H), 7.22 (s, 1H), 7.26-7.33 (m, 2H).

Example 9: 13-(2-fluorobenzoyl)-9,10-dimethoxy-5H-[1,3]dioxolo[4,5-g]isoquinolino[3,2-a]isoquinoline-8(6H)-one

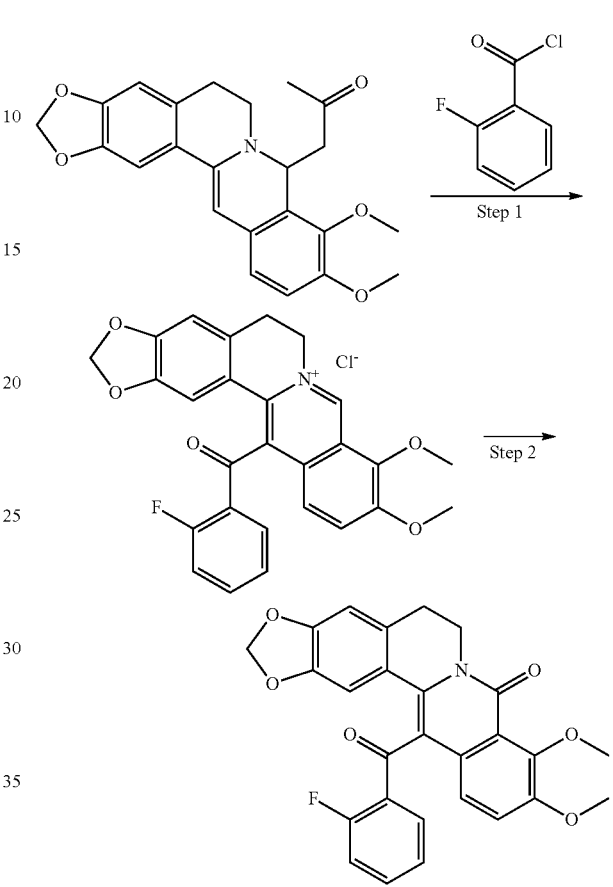

Step 1: 13-(2-fluorobenzoyl)-9,10-dimethoxy-5H-[1,3]dioxolo[4,5-g]isoquinolino[3,2-a]isoquinoline-iumchloride A target compound (60%) was obtained by the same manner as described in step 1) of Example 1 except that 2-fluorobenzoyl chloride was used instead of 2-fluorobenzyl bromide in step 1) of Example 1.

$^1$H NMR (300 MHz, CDCl$_3$) δ 3.18-3.47 (m, 2H), 4.04(s, 3H), 4.06(s, 3H), 4.40(s, 2H), 6.08 (s, 2H), 6.59(s, 1H), 6.95(s, 1H), 7.03-7.13 (m, 1H), 7.18-7.20(m, 1H), 7.42-7.60 (m, 2H), 7.69-7.77 (m, 1H), 7.82-7.87(m, 1H).

Step 2: 13-(2-fluorobenzoyl)-9,10-dimethoxy-5H-[1,3]dioxolo[4,5-g]isoquinolino[3,2-a]isoquinoline-8(6H)-one A target compound (15%) was obtained by the same manner as described in step 2) of Example 4 except that the 13-(2-fluorobenzoyl)-9,10-dimethoxy-5H-[1,3]dioxolo[4,5-g]isoquinolino[3,2-a]isoquinoline-iumchloride obtained in step 1) was used instead of 9,10-dimethoxy-13-(2-methylbenzyl)-5,6-dihydro-[1,3]dioxolo[4,5-g]isoquinolino [3,2-a]isoquinoline-7-iumbromide in Example 4.

$^1$H NMR (300 MHz, CDCl$_3$) δ 2.80 (m, 2H), 3.94 (s, 3H), 4.03 (s, 3H), 4.24(m, 2H), 5.88 (s, 2H), 6.59 (s, 1H), 6.866.92 (m, 1H), 6.97 (s, 1H), 7.02-7.07 (m, 1H), 7.29 (d, J=9.0 Hz, 1H), 7.34=7.39 (m, 1H), 7.49 (d, J=9.0 Hz, 1H), 7.63-7.68 (m, 1H)

Example 10: ethyl 9,10-dimethoxy-8-oxo-6,8-di-hydro-5H-[1,3]dioxolo[4,5-g]isoquinolino[3,2-a]isoquinoline-13-carboxylate

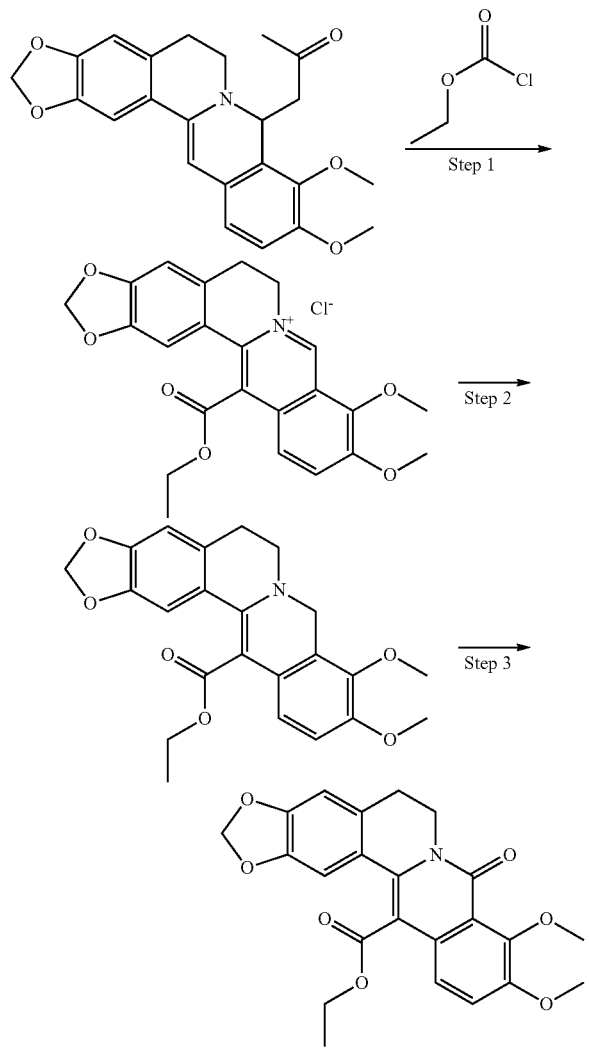

Step 1: 13-(ethoxycarbonyl)-9,10-dimethoxy-5,6-dihydro-[1,3]dioxolo[4,5-g]isoquinolino [3,2-a]isoquinoline-7-iumchloride A target compound (55%) was obtained by the same manner as described in step 1) of Example 1 except that ethyl chloroformate was used instead of 2-fluorobenzyl bromide in step 1) of Example 1.

$^1$H NMR (300 MHz, CDCl$_3$) δ 1.31 (t, J=6.9 Hz, 3H), 3.26-3.29 (m, 2H), 4.08(s, 3H), 4.38(s, 3H), 4.47 (q, J=6.9 Hz, 2H), 5.40 (m, 2H), 6.09 (s, 2H), 6.89 (s, 1H), 7.14 (s, 1H), 7.74 (d, J=9.3 Hz, 1H), 7.88 (d, J=9.0 Hz, 1H), 11.01 (s, 1H)

Step 2: ethyl 9,10-dimethoxy-6,8-dihydro-[1,3]dioxolo[4,5-g]isoquinolino [3,2-a]isoquinoline-13-carboxylate The 13-(ethoxycarbonyl)-9,10-dimethoxy-5,6-dihydro-[1,3]dioxolo[4,5-g]isoquinolino [3,2-a]isoquinoline-7-iumchloride (0.84 g, 1.89 mmol) obtained in step 1 was dissolved in methanol (50 mL), to which sodium borohydride (54 mg, 1.42 mmol) dissolved in 5 mL of 5% sodium hydroxide solution was slowly added at 0° C., followed by stirring for 1 hour. The reactant was extracted with ethyl acetate, dried over sodium sulfate, and concentrated. The residue was separated by flash column chromatography (ethyl acetate:hexane=1:3) to give the target compound (93%).

$^1$H NMR (300 MHz, CDCl$_3$) δ 1.14 (t, J=7.2 Hz, 3H), 2.80-2.84 (m, 2H), 3.23-3.26 (m, 2H), 3.81 (s, 3H), 3.84 (s, 3H), 4.14 (q, J=7.2 Hz, 2H), 4.51 (s, 2H), 5.93 (s, 2H), 6.62 (s, 1H), 6.93 (s, 1H), 6.81 (d, J=9.0 Hz, 1H), 7.38 (d, J=8.7 Hz, 1H)

Step 3: ethyl 9,10-dimethoxy-8-oxo-6,8-dihydro-5H-[1,3]dioxolo[4,5-g]isoquinolino[3,2-a]isoquinoline-13-carboxylate The ethyl 9,10-dimethoxy-6,8-dihydro-[1,3]dioxolo[4,5-g]isoquinolino [3,2-a]isoquinoline-13-carboxylate (0.8 g, 1.95 mmol) obtained in step 2) was dissolved in dichloromethane (300 mL), to which manganese dioxide (2 g, 23 mmol) was added, followed by reflux for 15 hours. Upon completion of the reaction, the excessive manganese dioxide was filtered out of the mixture, followed by concentration. The residue was separated by flash column chromatography to give the target compound (12%).

$^1$H NMR (300 MHz, CDCl$_3$) δ 1.23-1.28 (t, J=6.0 Hz, 3H), 2.86-2.90 (t, J=6.0 Hz, 2H), 3.95 (s, 3H), 3.99 (s, 3H), 4.20-4.24 (t, J=6.0 Hz, 2H), 4.30-3.37 (q, J=6.0 hz, 2H), 6.00 (s, 2H), 6.75 (s, 1H), 7.08 (s, 1H), 7.32-7.35 (d, J=9.0 Hz, 1H), 7.43-7.46 (d, J=9.0 Hz, 1H).

Example 11: 9,10-dimethoxy-8-oxo-6,8-dihydro-5H-[1,3]dioxolo[4,5-g]isoquinolino[3,2-a]isoquinoline-13-carboxylic acid

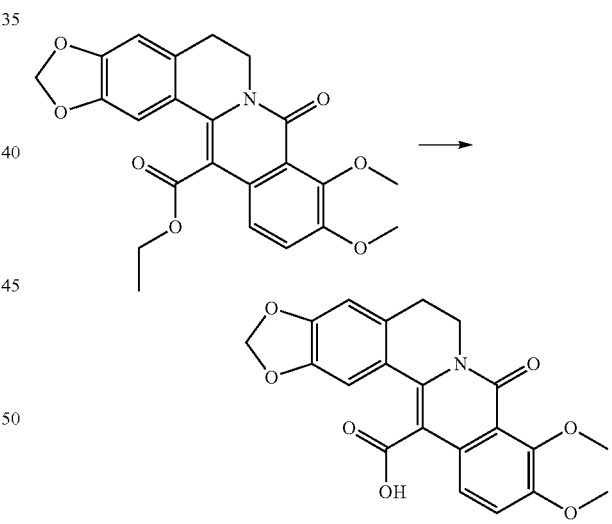

The ethyl 9,10-dimethoxy-8-oxo-6,8-dihydro-5H-[1,3]dioxolo[4,5-g]isoquinolino[3,2-a]isoquinoline-13-carboxylate (0.106 g, 0.25 mmol) obtained in Example 10 was added to 4 N sodium hydroxide solution (50 mL), followed, by stirring at 80° C. for 36 hours. The reactant was concentrated under reduced pressure, to which distilled water (20 mL) was added. PH of the mixture was regulated with 1 N HCl solution to make pH 4. The reactant was extracted with ethyl acetate, dried over sodium sulfate, and concentrated. The residue was separated by flash column chromatography (dichloromethane:methanol=10:1) to give the target compound (61 mg, 61%).

¹H NMR (300 MHz, DMSO-d₆) δ 2.81 (s, 2H), 3.76 (s, 3H), 3.88 (s, 3H), 4.03 (s, 2H), 6.08 (s, 2H), 6.98 (s, 1H), 7.29 (s, 1H), 7.36-7.39 (d, J=9.0 Hz, 1H), 7.55-7.58 (d, J=9.0 Hz, 1H).

Example 12: 9,10-dimethoxy-8-oxo-6,8-dihydro-5H-[1,3]dioxolo[4,5-g]isoquinolino[3,2-a]isoquinoline-13-carboxamide

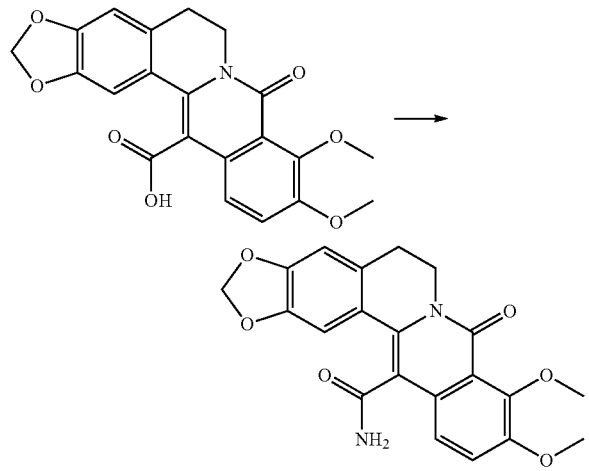

The 9,10-dimethoxy-8-oxo-6,8-dihydro-5H-[1,3]dioxolo[4,5-g]isoquinolino[3,2-a]isoquinoline-13-carboxylic acid (15 mg, 37.9 umol) obtained in Example 11 was dissolved in dichloromethane (10 mL), to which oxalate chloride (48 mg, 379 umol) was added, followed by stirring at room temperature for 2 hours. The reactant was concentrated and then dissolved in tetrahydrofuran (10 mL). The mixture was cooled down at 0° C., to which ammonia solution (28%, 5 mL) was added, followed by stirring for 1 hour. The reactant was extracted with ethyl acetate, dried over sodium sulfate, and concentrated. The residue was separated by flash column chromatography (dichloromethane:methanol=20:1) to give the target compound (7 mg, 47%).

¹H NMR (300 MHz, CDCl₃) δ 2.79-2.83 (t, J=6.0 Hz, 2H), 3.92 (s, 3H), 3.95 (s, 3H), 4.15 (s, 2H), 5.89 (s, 1H), 6.01 (s, 2H), 6.07 (s, 1H), 6.72 (s, 1H), 7.30-7.33 (d, J=9.0 Hz, 1H), 7.56-7.58 (m, 2H).

Example 13: N-(2-fluorophenyl)-9,10-dimethoxy-8-oxo-6,8-dihydro-5H-[1,3]dioxolo[4,5-g]isoquinolino[3,2-a]isoquinoline-13-carboxamide

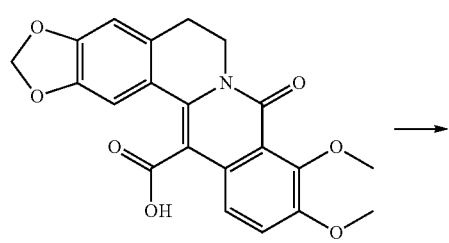

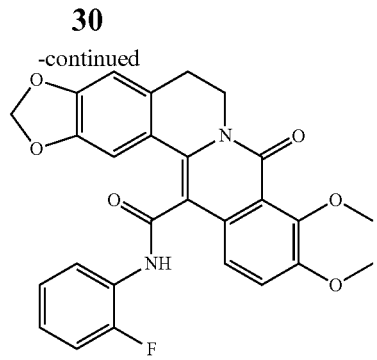

The 9,10-dimethoxy-8-oxo-6,8-dihydro-5H-[1,3]dioxolo[4,5-g]isoquinolino[3,2-a]isoquinoline-13-carboxamide (15 mg, 37.9 μmol) obtained in Example 12 was dissolved in dimethylformamide (3 mL), to which 2-fluoroaniline (5 μL, 45 μmol), 1-hydroxybenzotriazole (8 mg, 57 mol), diisopropylethylamine (16 μL, 95 μmol), and EDC (11 mg, 57 μmol) were added in that order, followed by stirring for 48 hours. Distilled water was added to the reactant. The reactant was extracted with ethyl acetate, dried over sodium sulfate, and concentrated. The residue was separated by flash column chromatography (ethyl acetate:hexane=1:1) to give the target compound (5 mg, 27%).

¹H NMR (300 MHz, CDCl₃) δ 2.96-3.00 (t, J=6.0 Hz, 2H), 3.99 (s, 3H), 4.04 (s, 3H), 4.28-4.32 (t, J=6.0 Hz, 2H), 6.13 (s, 2H), 6.85 (s, 1H), 7.08 (s, 1H), 7.32-7.57 (m, 5H), 7.73-7.76 (d, J=9.0 Hz, 1H), 8.07-8.10 (d, J=9.0 Hz, 1H).

Experimental Example 1: The Inhibitory Effect of the Compound of the Invention on the Expression of iNOS Gene To investigate whether or not the derivative of the present invention could inhibit iNOS inducement, Raw264.7 cells (mouse macrophages) were distributed in a 384-well plate at the density of 3×10⁴ cells/well. The cells were treated with LPS at the concentration of 100 ng/ml, followed by culture at 37° C. for 24 hours. The concentration of nitrate increased in the medium was measured by using Griess reagent. The inhibition rate was calculated by mathematical formula based on the detected signals. The results are shown in Table 2.

% inhibition=(mean value of sample−mean value of negative control)/(mean value of positive control −mean value of negative control)×100     [Mathematical Formula 1]

TABLE 2

| Example | Inhibition rate of iNOS induction (%) | |
|---|---|---|
| | 10 μM | 1 μM |
| 1 | 134.2 | 91.0 |
| 2 | 95.2 | 56.8 |
| 3 | 112.7 | 74.1 |
| 4 | 97.9 | 23.2 |
| 5 | 98.3 | 29.0 |
| 6 | 114.9 | 7.2 |
| 7 | 100.0 | 13.4 |
| 8 | 107.7 | 1.8 |
| 9 | 116.6 | 65.6 |
| 10 | 99.2 | 53.9 |
| 11 | 118.4 | −17.2 |
| 12 | 107.4 | 35.4 |
| 13 | 105.9 | 70.8 |

As shown in Table 2, the compound of the present invention was confirmed to have the activity to inhibit iNOS induction.

Therefore, the derivatives of the present invention can be efficiently used as a pharmaceutical composition for the prevention or treatment of iNOS induction related diseases.

Experimental Example 2: The Inhibitory Effect of the Compound of the Invention on the Transcriptional Activity of NFAT5

To investigate whether or not the derivative of the present invention could inhibit the transcriptional activity of NFAT5, NFAT5 reporter screening was performed. A plasmid vector was constructed by eliminating CMV promoter sequence from the backbone and inserting NFAT5 binding site sequence (TGGAAAATTACCG) instead. Raw264.7 cells transfected with the vector were cultured in 10% FBS-PRMI (supplemented with 500 μg/ml G418). The cells were distributed in a 96-well plate at the density of $3\times10^3$ cells/well, followed by further culture for one more day. The cells were treated with LPS at the concentration of 1 μg/ml for 48 hours. Then, the cells were fixed and the expression level of GFP was measured by HCS fluorescence image (Thermo, ArrayScan$^{VTI}$). The results are shown in Table 3 and FIG. 1.

FIG. 1 is a graph illustrating the inhibitory effect of the derivative of the present invention on the transcriptional activity of NFAT5

TABLE 3

| | Inhibition rate of NFAT5 transcription (%) | |
|---|---|---|
| Example | 10 μM | 1 μM |
| 1 | 81.2 | 11.2 |
| 2 | 24.4 | 13.6 |
| 3 | 108.8 | 24.6 |
| 4 | 88.2 | 7.4 |
| 5 | 77.6 | 24.2 |
| 6 | 67.9 | 9.9 |
| 7 | 28.2 | 18.5 |
| 8 | 67.3 | 15.7 |
| 9 | 16.4 | 0.5 |
| 10 | 53.7 | −3.8 |
| 11 | −12.8 | −10.4 |
| 12 | −5.2 | −2.9 |
| 13 | −29.9 | −11.1 |

As shown in Table 3 and FIG. 1, the derivatives of the present invention were confirmed to be excellent in inhibiting NFAT5 activity and particularly the derivatives of Examples 1, 3, 6, and 10 were remarkably excellent in inhibiting NFAT5 activity. Therefore, the derivatives of the present invention can be used as a pharmaceutical composition for the prevention or treatment of NFAT5 activity related diseases.

Experimental Example 3: Evaluation of the Effect of the Compound of the Invention on the Transcriptional Activity of NF-kB, NFATc, CREB, and ELK The following experiment was performed to investigate the effect of the compounds of the present invention on the transcriptional activity of NF-κB, NFATc, CREB, and ELK in addition to NFAT.

Particularly, in order to measure the transcriptional activity of NF-kB, THP1-Lucia NF-kB reporter cells were cultured in 10% FBS-RPMI medium (supplemented with 100 ug/ml of Zeocin). The cells were cultured in a 96-well plate at the density of $2\times10^4$ cells/well, to which 1 μg/ml of LPS and the compound of the invention were added. The cells were cultured for 24 hours. 10 μl of the supernatant was added with 50 μl of fluorescence reagent. Then, luminescence was measured.

To evaluate the transcriptional activity of NFAT, THP1-XBlue-MD2-CD14 cells were cultured in 10% FBS-RPMI (supplemented with 200 μg/ml of Zeocin and 250 μg/ml of G418). First, the cells were distributed in a 96-well plate at the density of $2\times10^4$ cells/well, followed by culture. 1 μg/ml of LPS and the compound of the invention were added thereto, followed by culture for 24 hours. 20 μl of the supernatant was added with 180 μl of secreted embryonic alkaline phosphatase (SEAP) detection medium, followed by culture for 2 hours. Then, $OD_{655}$ was measured.

Further, to evaluate the transcriptional activity of CREB and ELK1, CHO/CREB-luc, HEK293/CREB-luc, and HLR/ELK1 cells were used. The cells were respectively cultured in 10% FBS-F12 (supplemented with 100 μg/ml of hygromycin), 10% FBS-DMEM (supplemented with 100 μg/ml of hygromycin), and 10% FBS-DMEM (supplemented with 200 μg/ml of G418), which were distributed in a 96-well plate at the density of $1\times10^4$ cells/well, followed by culture for one more day. The cells treated with 10 μM Forskolin or 1 μg/ml of PMA were homogenized, to which 25 μl of luminescence detection reagent was added. Then, luminescence was measured.

Figure 2:
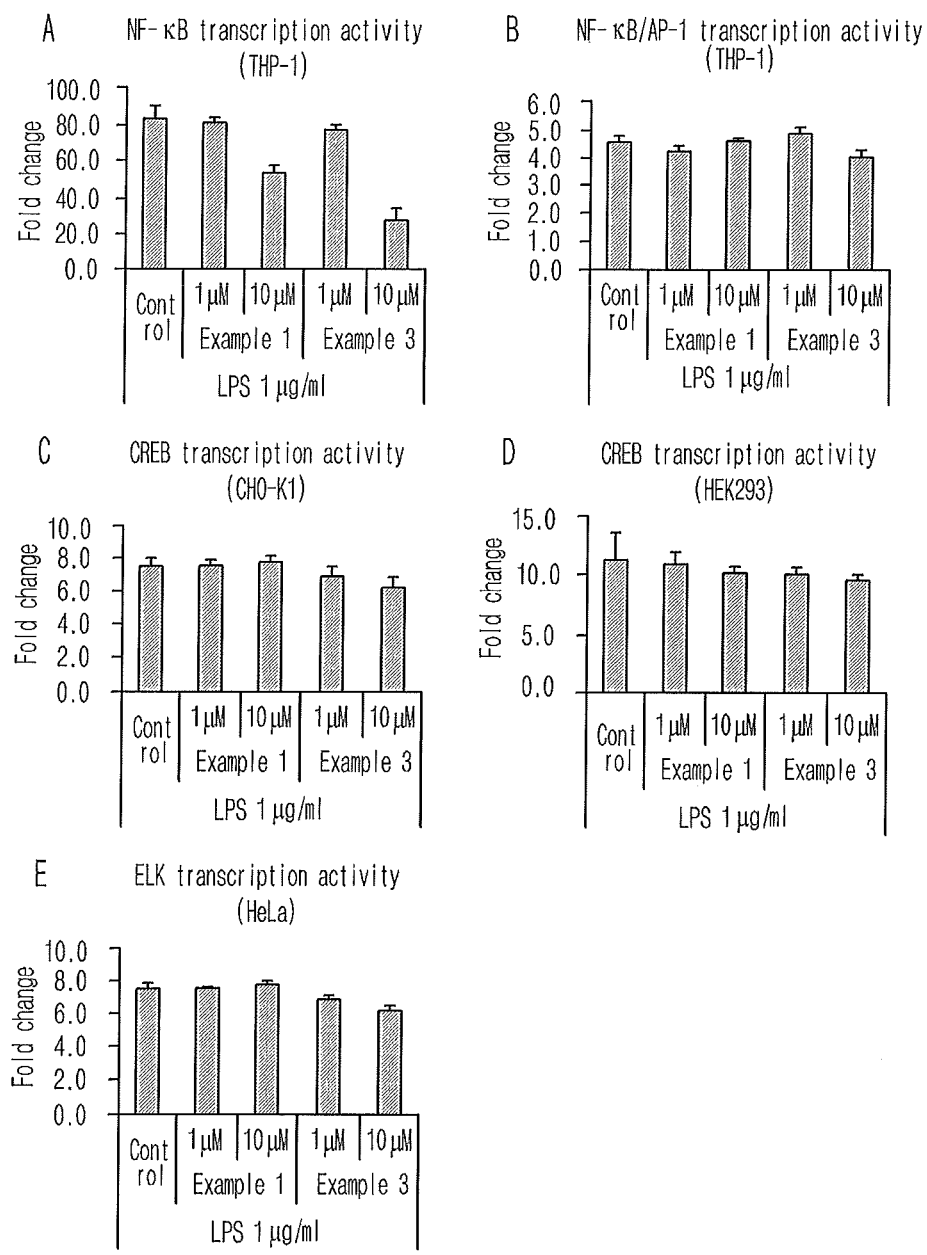
FIG. 2 is a graph illustrating the effect of the derivative of the present invention on the transcription activity of other transcription factors in addition to NFAT, wherein A is NF-κB, B is NFATc, C is CREB (CHO-K1), D is CREB (HEK293), and E is ELK.

FIG. 2 is a graph illustrating the effect of the derivative of the present invention on the transcription activity of other transcription factors in addition to NFAT, wherein A is NF-κB, B is NFATc, C is CREB (CHO-K1), D is CREB (HEK293), and E is ELK.

As shown in FIG. 2, the protoberberine derivative of the present invention was confirmed to inhibit NFAT5 at least 80% at the concentration of 1 μM. However, such inhibitory effect of the derivative of the invention was not as much significant for other transcription factors. The derivatives of Example 1 and Example 3 were observed to inhibit NF-kB and NFAT promoter activity slightly.

Therefore, the protoberberine derivative of the present invention was confirmed to inhibit selectively the transcriptional activity of NFAT5.

Experimental Example 4: Evaluation of the Effect of the Compound of the Invention on the Transcriptional Activity of p38

To confirm the effect of the derivative of the present invention on the phosphorylation of p38, RAW264.7 cells were cultured in a 12-well plate at the density of $1.5\times10^5$ cells/well in 10% FBS-RPMI 1640 medium. The cells were treated with 1 μM of the compound of Example 1 or not treated. The cells were stimulated with LPS at the concentration of 1 μg/ml. Then, Western blotting was performed to investigate the activation (phosphorylation) of p38 protein according to the treating period of LPS (15, 30, and 60 minutes).

Figure 3:
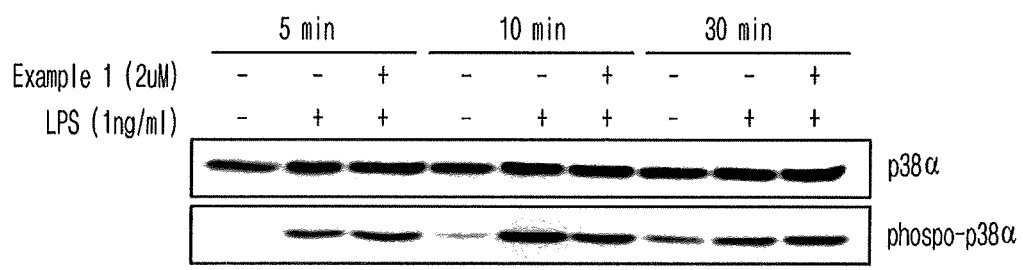
FIG. 3 presents the image of Western blotting illustrating the effect of the derivative of the present invention on the expression (phosphorylation) of p38 protein.

FIG. 3 presents the image of Western blotting illustrating the effect of the derivative of the present invention on the expression (phosphorylation) of p38 protein As shown in FIG. 3, the expression (phosphorylation) of p38 protein was not different between the experimental group treated with the derivative of the invention and the control not treated with the derivative.

Experimental Example 5: Investigation of NFAT5 Transcription and Nuclear Localization It was investigated whether or not the derivative of the present invention could affect the expression of NFAT5 mRNA.

Particularly, RAW264.7 cells were distributed in a 12-well plate at the density of $1.5 \times 10^5$ cells/well, followed by culture in 10% FBS-RPMI 1640 medium. The cells were stabilized for a day. The compound of Example 1 was treated thereto at the concentration of 1 μM for 1 hour, and then the cells were stimulated with LPS for 12 hours. 12 hours later, mRNA was extracted from the cells, and cDNA was synthesized therefrom. PCR (real-time PCR) was performed to measure the expression level of NFAT5 mRNA. The migration of the transcription factor NFAT5 from the cytoplasm to the nucleus was investigated. Particularly, RAW264.7 cells were distributed in a 6-well plate at the density of $6 \times 10^5$ cells/well, followed by culture in 10% FBS-RPMI 1640 medium. The cells were pre-treated with the compound 6 (1 μM) for 1 hour, and treated with LPS (1 μg/ml) for 24 hours. Cytoplasm and nucleus proteins were separated from the stimulated cells and the levels of NFAT5 and p65 protein (NF-kB subunit) were measured. The results are shown in FIG. 4.

Figure 4:
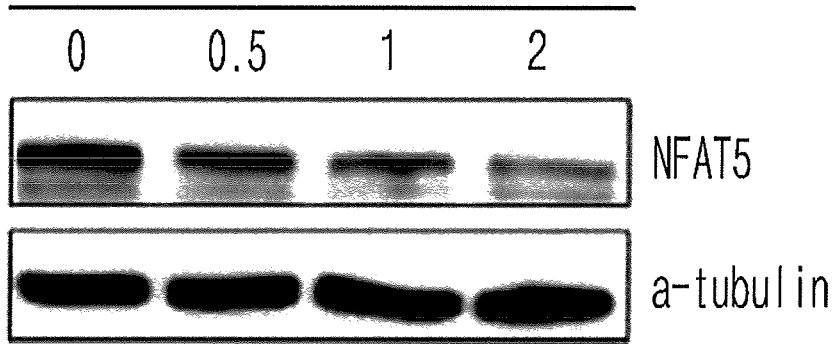
FIG. 4 is a graph illustrating the effect of the derivative of the present invention on the transcription and nuclear localization.

FIG. 4 is a graph illustrating the effect of the derivative of the present invention on the transcription and nuclear localization As shown in FIG. 4, the expression of NFAT5 induced by LPS was more increased in the protein separated from the nucleus than in the protein separated from the cytoplasm. In the cells pre-treated with the compound of Example 1, the protein level increased by the treatment of LPS was reduced.

Therefore, it was confirmed that the increase of NAFT5 expression caused by LPS could be suppressed by the compound of Example 1 since the compound of Example 1 could inhibit the expression of NFAT5 protein from the phase of transcript.

Experimental Example 6: Effect on the Factors Reacting Under the Hypertonic Condition It was investigated whether or not the factors regulated by NFAT5 under the hypertonic condition could be affected by the compound of Example 1. Particularly, RAW264.7 cells were distributed in a 6-well plate at the density of $1.5 \times 10^5$ cells/well, followed by culture and stabilization in 10% FBS-RPMI 1640 medium. The cells were pre-treated with the compound of Example 1 (1 μM) for 1 hour, and then stimulated with NaCl (45 mM) for 3 hours. mRNA was extracted from the cells, from which cDNA was synthesized. Real-time PCR was performed with NFAT5 transcript and the results are shown in FIG. 5.

Figure 5:
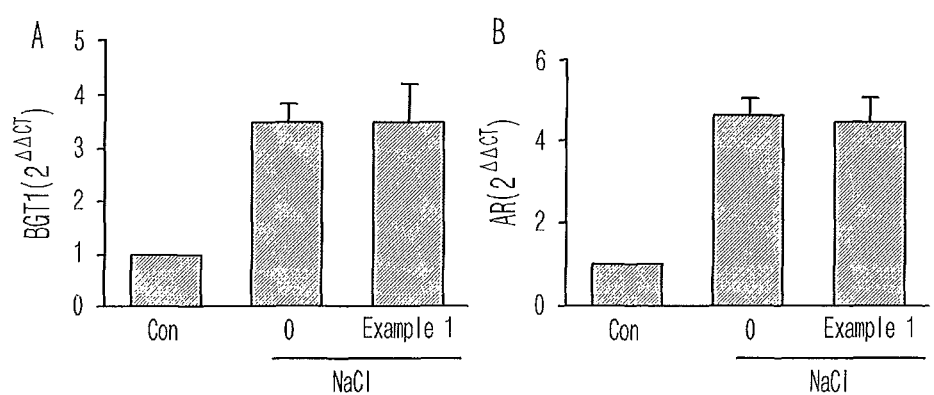
FIG. 5 is a graph illustrating the effect of the derivative of the present invention on the sodium chloride mediated up-regulation of NFAT5 transcript, wherein A indicates BGT1 and B indicates AR transcript.

FIG. 5 is a graph illustrating the effect of the derivative of the present invention on the sodium chloride mediated up-regulation of NFAT5 transcript, wherein A indicates BGT1 and B indicates AR transcript.

As shown in FIG. 5, when the cells were pre-treated with NaCl, the expression of the NAFT5 transcript BGT1 and AR was increased. The up-regulation of the transcript thereby was not changed by the treatment of the compound of Example 1.

Experimental Example 1: Inhibition of COX

To investigate whether or not the compound of the present invention could inhibit COX1 and COX2 enzymes (representative anti-inflammatory mechanism), the inhibition rate of the compound of Example 1 was compared with that of berberine.

Particularly, COX assay kit (Cat#760111, Cayman Co.) was used for the experiment. 69 μl of buffer, 5 μl of Heme, and 5 μl of the enzyme were mixed altogether with 1 μl of the compound of Example 1, followed by reaction at room temperature for 5 minutes. 10 μl of substrate and 10 μl of arachidonic acid were added thereto, followed by reaction for 10 minutes in the darkness. Then, $OD_{590}$ was measured. The results are shown in Tables 4 and 5.

TABLE 4

| Conc. (μM) | Indometacin | | Berberine | | Example 1 | |
|---|---|---|---|---|---|---|
| 100 | 101.7 | 90.6 | 53.5 | 51.5 | 28.4 | 23.4 |
| 20 | 93.6 | 86.6 | 24.4 | 31.4 | 11.4 | 7.4 |
| 4 | 72.6 | 71.6 | 18.4 | 20.4 | -6.7 | -10.7 |
| 0.8 | 62.5 | 66.6 | 12.4 | 13.4 | -4.7 | -2.7 |
| 0.16 | 41.5 | 39.5 | 3.3 | 5.4 | -1.7 | -7.7 |
| 0.032 | 17.4 | 15.4 | 2.3 | 0 | -14.7 | -18.7 |
| 0.0064 | 11.4 | 8.4 | — | — | — | — |
| 0.00128 | 2.3 | 0 | — | — | — | — |
| $IC_{50}$ (μM) | 0.38 | | 96.3 | | >100 | |

TABLE 5

| Conc. (μM) | Indometacin | | Berberine | | Example 1 | |
|---|---|---|---|---|---|---|
| 100 | 104.5 | 96.9 | 50.3 | 53.7 | 36.7 | 25.7 |
| 20 | 83.3 | 84.2 | 41.0 | 39.3 | 12.1 | 15.5 |
| 4 | 75.7 | 75.7 | 28.2 | 29.9 | 1.1 | -0.6 |
| 0.8 | 63.8 | 65.5 | 17.2 | 19.8 | -7.3 | -9.9 |
| 0.16 | 54.5 | 40.1 | 8.8 | 7.9 | -15.0 | -13.3 |
| 0.032 | 26.6 | 31.6 | 0 | 0 | -20.1 | -22.6 |
| 0.0064 | 9.6 | 8.8 | — | — | — | — |
| 0.00128 | 0 | 0 | — | — | — | — |
| $IC_{50}$ (μM) | 0.26 | | 58.4 | | >100 | |

As shown in Tables 4 and 5, the compound of Example 1 of the present invention displayed a weak inhibitory effect on COX1 and COX2.

Experimental Example 8: Cytotoxicity Test

To investigate the cytotoxicity of the derivative of the present invention, 5 kinds of cell lines (VERO: African green monkey kidney cell line, HFL-1: human embryonic lung cell line, L929: NCTC clone 929, mouse fibroblast cell line, NIH 3T3: mouse embryonic fibroblast cell line, and CHO-K1: Chinese hamster ovary cell line) were distributed in a 96-well plate at the density of $1 \times 10^4$ cells/well, which were treated with the compound of the present invention for 24 hours. The water-soluble tetrazolium salt WST-8 was added thereto. The orange colored formazan dye degraded by dehydrogenase in the live cells was read, followed by nonlinear regression to determine 50% growth inhibition concentration. The results are shown in Table 6.

TABLE 6

| | $GI_{50}$ (μM) | | | | |
|---|---|---|---|---|---|
| Compound | VERO | L929 | HFL-1 | NIN3T3 | CHO-K1 |
| 1 | 84.2 | 40.3 | 26.1 | 7.16 | 12.1 |
| 3 | 84.9 | 47.7 | 32.8 | 10.2 | 16.7 |
| 6 | >100 | >100 | >100 | >100 | >100 |
| 8 | >100 | >100 | >100 | >100 | >100 |

As shown in Table 6, the derivative of the present invention was confirmed not to have a significant cytotoxicity on cells at the concentration of 10 μM or under.

Experimental Example 9: Inhibitory Effect on the Secretion of Inflammatory Cytokines To investigate whether or not the derivative of the present invention could affect the expressions of the NFAT5 target genes GM-CSF2, MCP-1, and IL-6, real time PCR, ELISA, and Western blotting were performed. Particularly, Raw264.7 cells were distributed in a 12-well plate at the density of $1.5 \times 10^6$ cells/well, followed by culture in 10% FES-PRMI medium. On the next day, the cells were pre-treated with the compound of Example 1 at the concentration of 1 μM for 1 hour, followed by LPS treatment (1 μg/ml) for 6 hours. Then, the supernatant was collected and the levels of GM-CSF, MCP-1, and IL-6 were measured by ELISA. The results are shown in FIG. 6.

Figure 6:
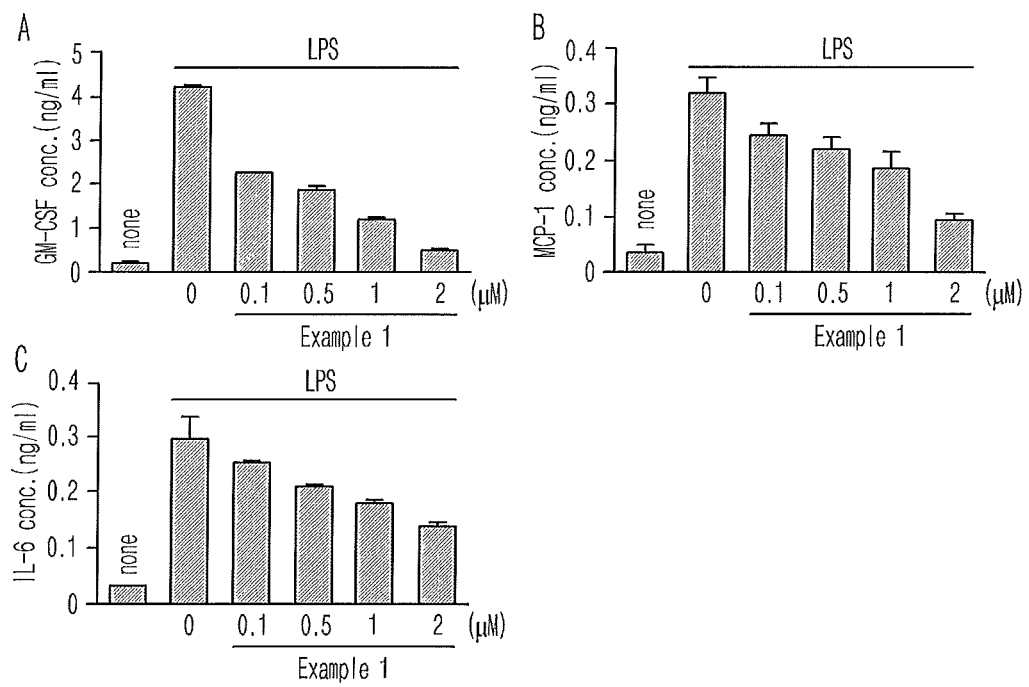
FIG. 6 is a graph illustrating the inhibitory effect of the derivative of the present invention on inflammatory cytokine, wherein A indicates GM-CSF2, B indicates MCP-1, and C indicates IL-6.

FIG. 6 is a graph illustrating the inhibitory effect of the derivative of the present invention on inflammatory cytokine, wherein A indicates GM-CSF2, B indicates MCP-1, and C indicates IL-6.

As shown in FIG. 6, the expressions of GM-CSF2, MCP-1, and IL-6 proteins increased by LPS were significantly reduced by the treatment of the derivative of the present invention.

Experimental Example 10: Experiment with the Mouse Model Having Rheumatoid Arthritis Induced by Collagen The following experiment was performed to investigate whether or not the compound of Example 1 of the present invention could inhibit the development of arthritis in vivo.

Particularly, male DBA/1 mice (Jackson Laboratories, Bar Harbor, Me.) at 7-8 weeks were treated with bovine type II collagen (CII: Chondrex, Redmond, Wash.) to induce immune response therein. 3 weeks later, the mice were oral-administered with the compound of Example 1 (15 mg/kg, 60 mg/kg) three times a week for 5 weeks. Points for the symptoms were given based on the standard set as follows: 0=normal, 1=very weak, 2=weak, 3=ordinary, 4—severe. Arthritis on the mouse leg was observed for 5 weeks during which the compound of Example 1 was continuously administered and the results of the evaluation are shown in FIG. 7.

Ankle score={sum of the evaluation scores of all other legs except the immune reaction induced leg (all mice)}/mouse number(n)  [Mathematical Formula 2]

Figure 7:
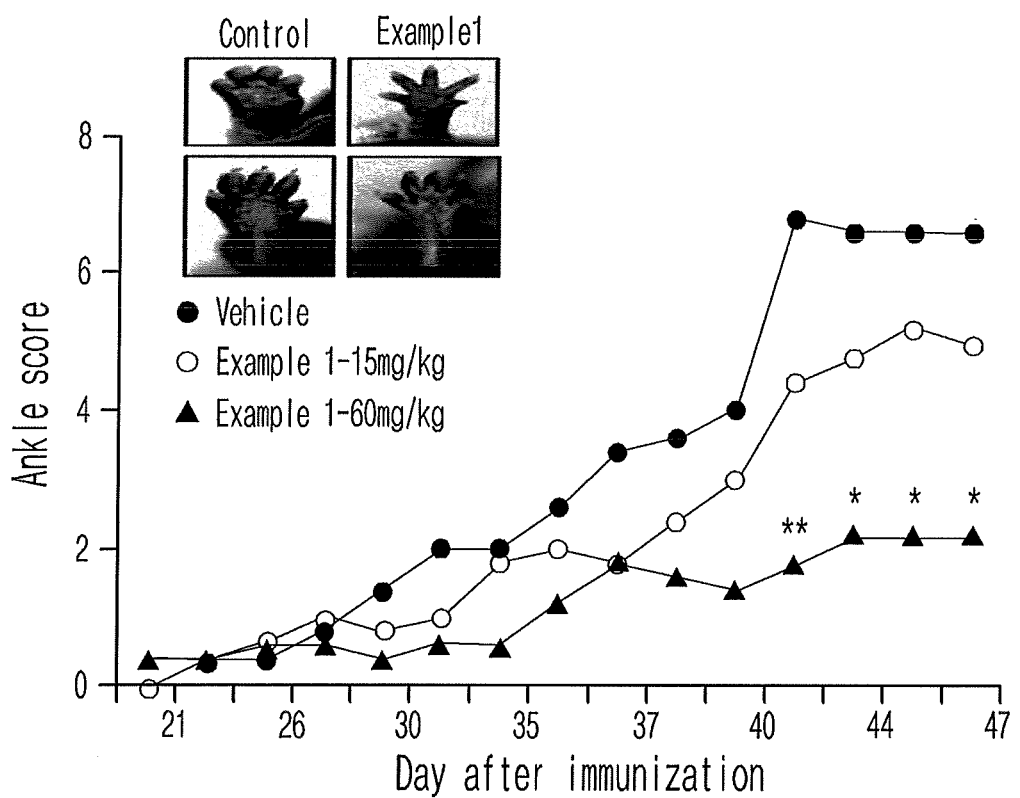
FIG. 7 is a graph illustrating the effect of the derivative of the present invention on immune response, which also presents the photograph illustrating before (control) and after the administration of the derivative of the invention to the joint of a mouse leg.

As a result, as shown in FIG. 7, compared with the negative control, arthritis symptoms in the experimental group mouse leg was relieved, confirmed by the observation with the naked eye. Histological staining also confirmed that arthritis symptoms were significantly improved.

Therefore, it was confirmed that the derivative of the present invention could be useful as a pharmaceutical composition for the prevention or treatment of arthritis.

Experimental Example 11: The Expressions of Inflammatory Cytokines in the Mouse Model Having Rheumatoid Arthritis Induced by Collagen The following experiment was performed to investigate the expressions of inflammatory cytokines in the mouse model having rheumatoid arthritis.

Particularly, the mice having arthritis induced by collagen in Example 10 were used herein. Cells were extracted from the mouse spleen, which were cultured in a 12-well plate and stabilized. Cells were stimulated with LPS for 12 hours and the expressions of inflammatory cytokines (TNF-α, IL-6) were measured by ELISA.

Figure 8:
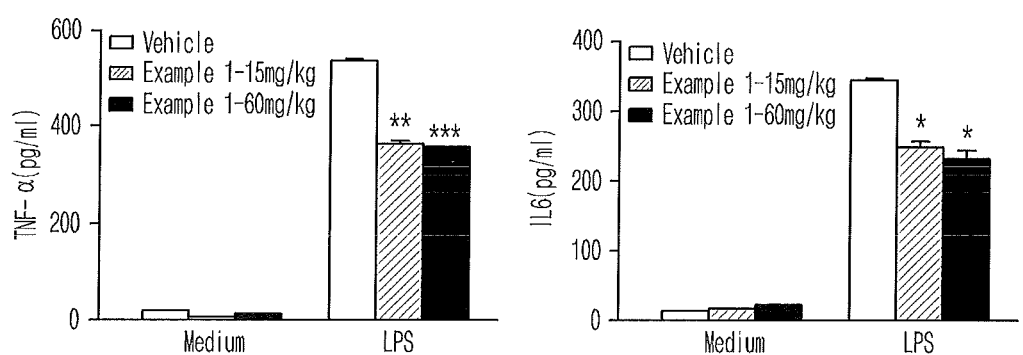
FIG. 8 is a diagram illustrating the inhibitory effect of the compound of 1 on the expression of inflammatory cytokines (TNF-α, IL-6) induced by LPS in a mouse having rheumatoid arthritis induced by collagen.

As a result, as shown in FIG. 8, when the arthritis mouse spleen cells were stimulated with LPS, the expressions of inflammatory cytokines (TNF-α, IL-6) were increased, compared with the group treated with the medium alone. The expression level of TNF-α was 530 (μg/ml) and the expression level of IL-6 was 400 (μg/ml). However, when the compound of Example 1 was treated to those cells respectively at the concentrations of 15 and 60 mg/kg, the expressions of TNF-α and IL-6 were reduced.

Experimental Example 12: The Expression of NFAT5 in the Mouse Model Having Rheumatoid Arthritis Induced by Collagen The following experiment was performed to investigate the expression of NFAT5 protein in the mouse model having rheumatoid arthritis.

Particularly, the spleen cells of the mouse having arthritis induced by collagen by the same manner as described in Example 11 were stimulated with LPS. Protein was extracted from the cells, followed by quantification of NFAT5 protein.

Figure 9:
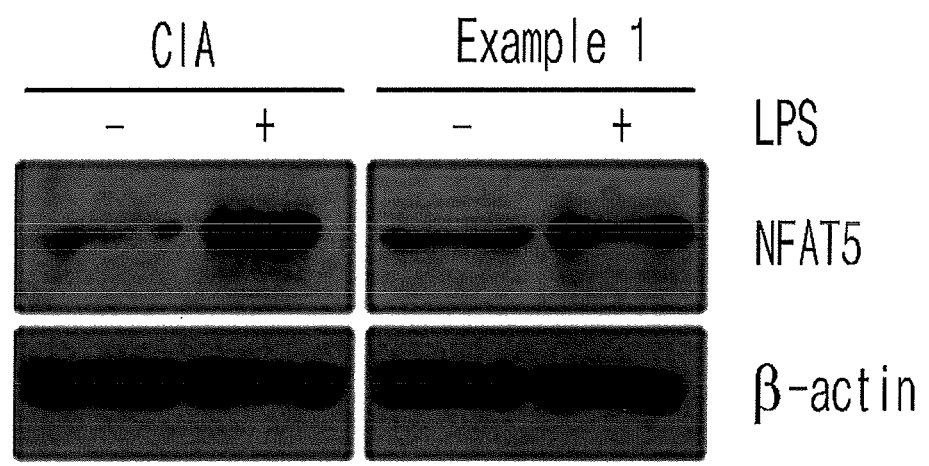
FIG. 9 is a diagram illustrating the inhibitory effect of the compound of 1 on the expression of NFAT induced by LPS in a mouse having rheumatoid arthritis induced by collagen.

As a result, as shown in FIG. 9, the expression of NFAT5 was increased in the CIA (Collagen Induced Arthritis) group treated with LPS, however, the expression of NFAT5 was suppressed by the treatment of the compound of Example 1.

Experimental Example 13: Investigation of Metabolic Stability and Pharmacokinetics in Liver Microsomes To investigate the metabolic stability and pharmacokinetics of the compounds of Example 1 and Example 3, the following experiment was performed.

Particularly, each compound was added to rat and human liver microsome fractions, followed by culture for 30 minutes. Then, the remaining compound was measured and the results are shown in Table 7. Each compound was administered via intravenous injection (iv) and oral-administration (po) to rat at the concentration of 5 mg/kg, followed by making pharmacokinetic profiles. The results are shown in FIGS. 10a and 10b.

Figure 10A:
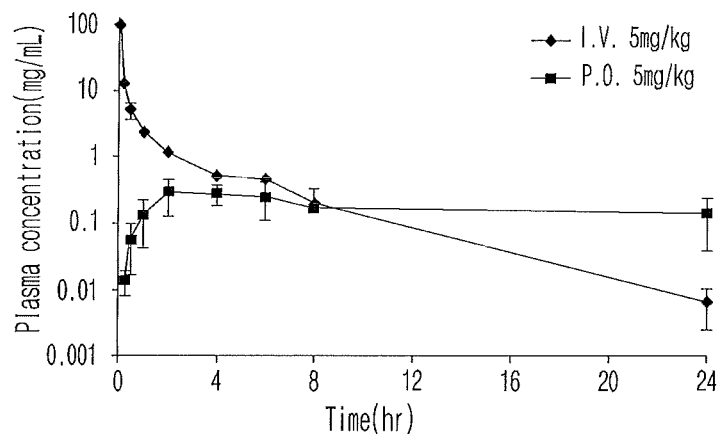
FIG. 10a and FIG. 10b are diagrams illustrating the metabolic stability and pharmacokinetics in the liver microsomes according to the compounds of 1 and 3.
Figure 10B:
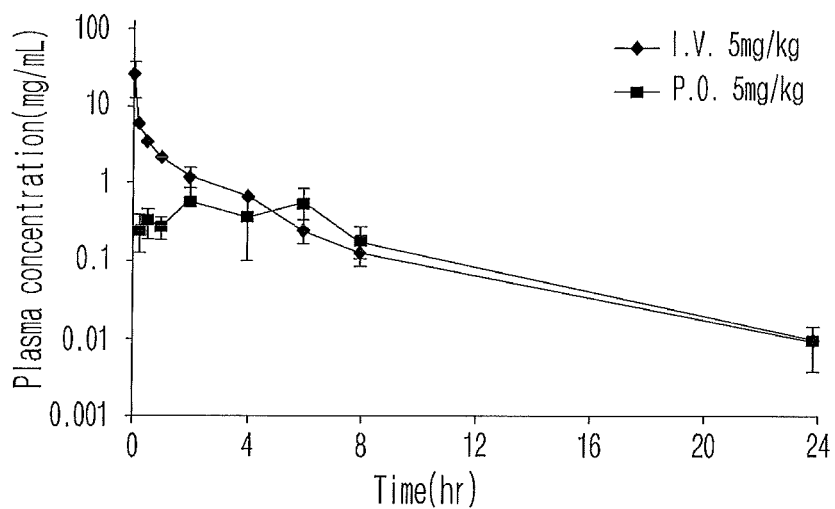

As a result, as shown in Table 7, FIG. 10a, and FIG. 10b, the oral absorption rate was significantly increased due to the improvement of physical properties of 8-oxo derivative, compared with protoberberine derivative.

TABLE 7

| Compound | Rat (%) | Human (%) |
|---|---|---|
| Example 1 | 35 ± 3 | 68.2 ± 6.1 |
| Example 3 | 18.5 ± 5.2 | 63.7 ± 2.4 |
| Control (buspirione) | 0.82 ± 0.16 | 3.88 ± 0.24 |

Experimental Example 1: Inhibitory Effect of the Compound of the Invention on the Secretion of Inflammatory Cytokines in Human Mononuclear Cells The following experiment was performed to investigate whether or not the compound of the present invention could inhibit the secretion of inflammatory cytokines in human mononuclear cells.

Particularly, PBMC separated from healthy human blood was treated with LPS (1 μg/ml). The cells were treated with the compound of the present invention at the concentration of 1 μg/ml, followed by culture for 6 hours to investigate whether or not the induced inflammatory cytokine secretion was inhibited by the compound. RNA was separated from the cells, from which the transcription levels of IL-6 and TNF-α were quantified by real-time PCR. The results are shown in FIG. 11 (NC: negative control, PC: positive control).

Figure 11:
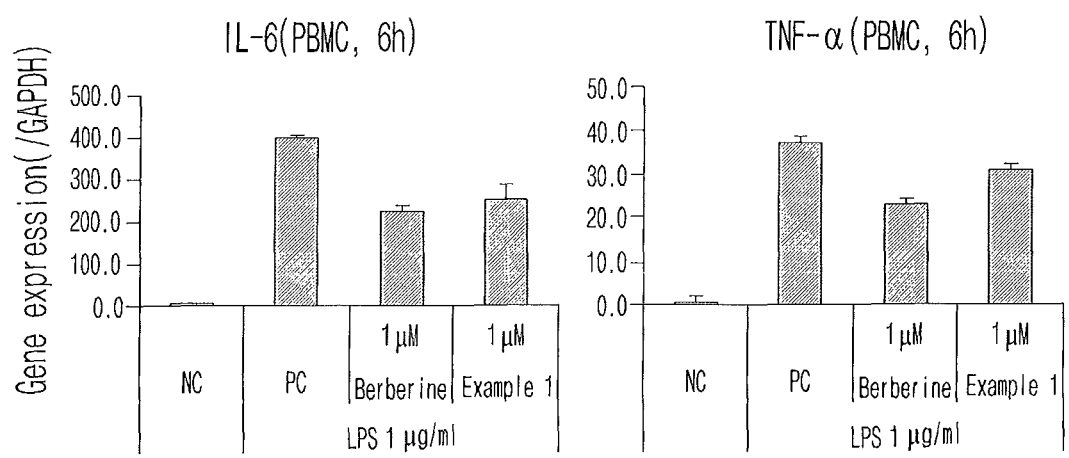
FIG. 11 is a diagram illustrating the inhibitory effect of the compound of 1 on the secretion of inflammatory cytokine in human mononuclear cells.

As a result, as show in FIG. 11, it was confirmed that the compound of Example 1, the NFAT5 inhibitor, could inhibit the expression of cytokines.

Experimental Example 15: Inhibition of Differentiation of Mouse T Cells into Th17 Cells The following experiment was performed to investigate whether or not the compound of Example 1 could inhibit the differentiation of Th17 cells.

Particularly, the transgenic mouse (Rag2 KO/OVA-TCRtg) naïve T cells were cultured under the condition of Th17 cell differentiation (treated with IL-6, IL-1β, and TGF-β along with APC cells) for 3 days. Compared with berberine known as a Th17 differentiation inhibitor, the inhibitory effect of the NFAT5 inhibitor on the differentiation of Th17 was measured by quantifying the secreted cytokine protein. Cell survival rate under the same condition was also measured by CCK-8.

Figure 12:
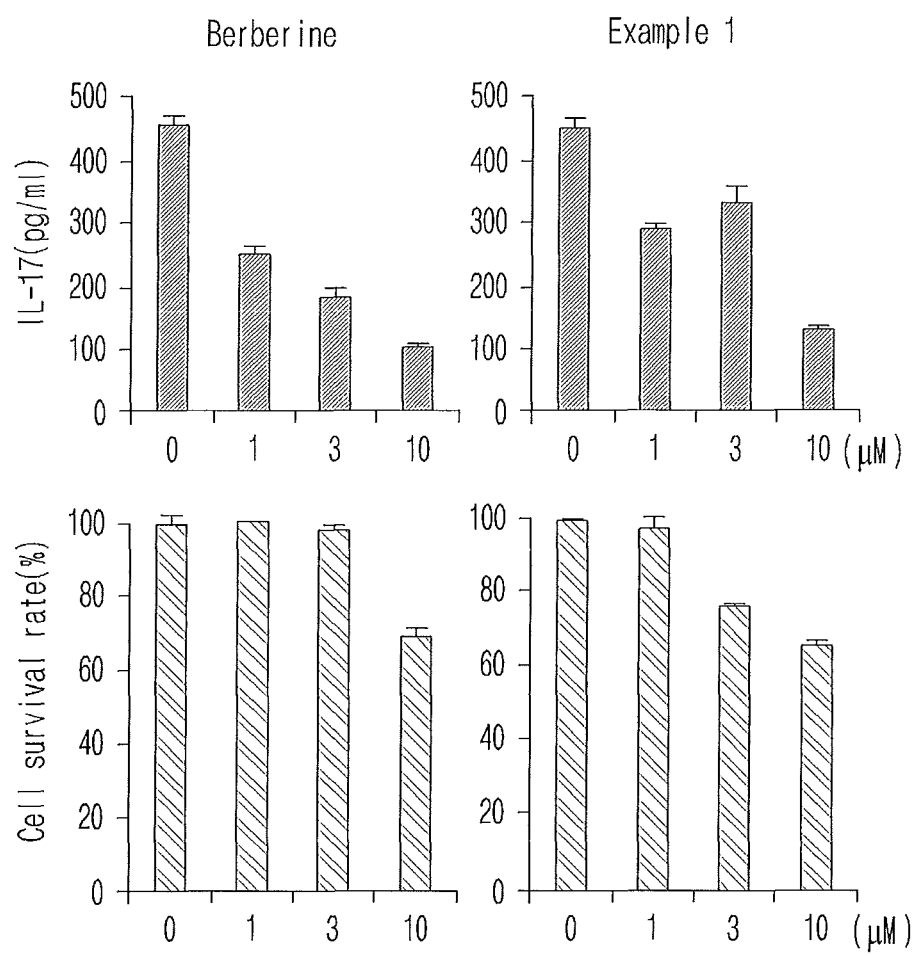
FIG. 12 is a diagram illustrating the inhibitory effect of the compound of 1 on the differentiation of Th17 cells.

As a result, as shown in FIG. 12, the compound of Example 1 demonstrated the inhibitory effect on the differentiation of Th17 as similar as berberine.

Manufacturing Example 1: Preparation of Pharmaceutical Formulations

<1-1> Preparation of Powders

| Derivative of formula 1 | 2 g |
|---|---|
| Lactose | 1 g |

Powders were prepared by mixing all the above components, which were filled in airtight packs according to the conventional method for preparing powders.

<1-2> Preparation of Tablets

| Derivative of formula 1 | 100 mg |
|---|---|
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| Derivative of formula 1 | 100 mg |
|---|---|
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Injectable Solutions

| Derivative of formula 1 | 10 μg/Ml |
|---|---|
| Weak HCl BP | until pH 3.5 |
| Injectable NaCl BP | up to 1 Ml |

The compound of the present invention was dissolved in proper volume of injectable NaCl BP. pH of the prepared solution was regulated as 3.5 by using weak HCl BP. The volume was adjusted by using injectable NaCl BP. The solution was well mixed and filled in 5 Ml type I transparent glass ampoules. The ampoules were sealed by melting the glass of opening, followed by autoclave at 121° C. for at least 15 minutes for sterilization.

Manufacturing Example 2: Preparation of Health Functional Food

| Derivative of formula 1 | 500 ng |
|---|---|
| Vitamin complex | proper amount |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 mg |
| Calcium pantothenate | 0.5 mg |
| Minerals | proper amount |
| Ferrous sulfate | 1.75 mg |
| Zinc oxide | 0.82 mg |
| Magnesium carbonate | 25.3 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Vitamins and minerals were mixed according to the preferable composition rate for health food. However, the composition rate can be adjusted. The constituents were mixed according to the conventional method for preparing health functional food and then the composition for health functional food was prepared according to the conventional method.

Manufacturing Example 3: Preparation of Beverages

| Derivative of formula 1 | 500 ng |
|---|---|
| Citric acid | 1000 mg |
| Oligosaccharide | 100 g |
| Maesil (Prunus mume) Extract | 2 g |
| Taurine | 1 g |
| Purified water | up to 900 Ml |

The above constituents were mixed according to the conventional method for preparing health beverages. The mixture was heated at 85° C. for 1 hour with stirring and then filtered. The filtrate was loaded in sterilized containers, which were sealed and sterilized again, stored in a refrigerator until they would be used for the preparation of a composition for health beverages.

The constituents appropriate for favorite beverages were mixed according to the preferred mixing ratio but the composition ratio can be adjusted according to regional and national preferences, etc.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. An 8-oxoprotoberberine derivative represented by formula 1 or a pharmaceutically acceptable salt thereof

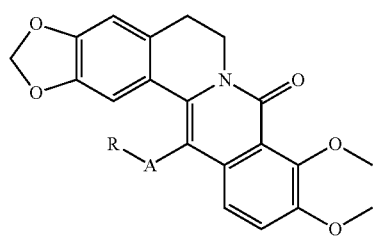

wherein A is —C(=O)— or —NHC(=O)—; and
when A is —C(=O)—, R is hydroxyl, amino, straight or branched C1-2 alkoxy, or phenyl unsubstituted or substituted with one or more halogens; and
when A is —NHC(=O)—, R is phenyl unsubstituted or substituted with one or more halogens, and
wherein said 8-oxoprotoberberine derivative or pharmaceutically acceptable salt thereof inhibits NFAT5.

2. The 8-oxoprotoberberine derivative according to claim 1, wherein the 8-oxoprotoberberine derivative is selected from the group consisting of:
13-ethyl-9,10-dimethoxy-8-oxo-6,8-dihydro-5H -[1,3]dioxolo[4,5-g]isoquinolino[3,2-a]isoquinoline-13-carboxylate;
9,10-dimethoxy-8-oxo-6,8-dihydro-5H-[1,3]dioxolo[4,5-g]isoquinolino[3,2-a]isoquinoline-13-carboxylic acid;
9,10-dimethoxy-8-oxo-6,8-dihydro-5H-[1,3]dioxolo[4,5-g]isoquinolino[3,2-a]isoquinoline-13-carboxamide; and
N-(2-fluorophenyl)-9,10-dimethoxy-8-oxo-6,8-dihydro-5H-[1,3]dioxolo[4,5-g]isoquinolino[3,2-a]isoquinoline-13-carboxamide.

3. A method for preparing the 8-oxoprotoberberine derivative of claim 1 represented by formula 1 comprising the following steps as shown in reaction formula 1:
preparing the compound represented by formula 4 by reacting the compound represented by formula 2 with the compound represented by formula 3 (step 1); and
preparing the compound represented by formula 1 by reacting the compound represented by formula 4 obtained in step 1) under basic condition (step 2):

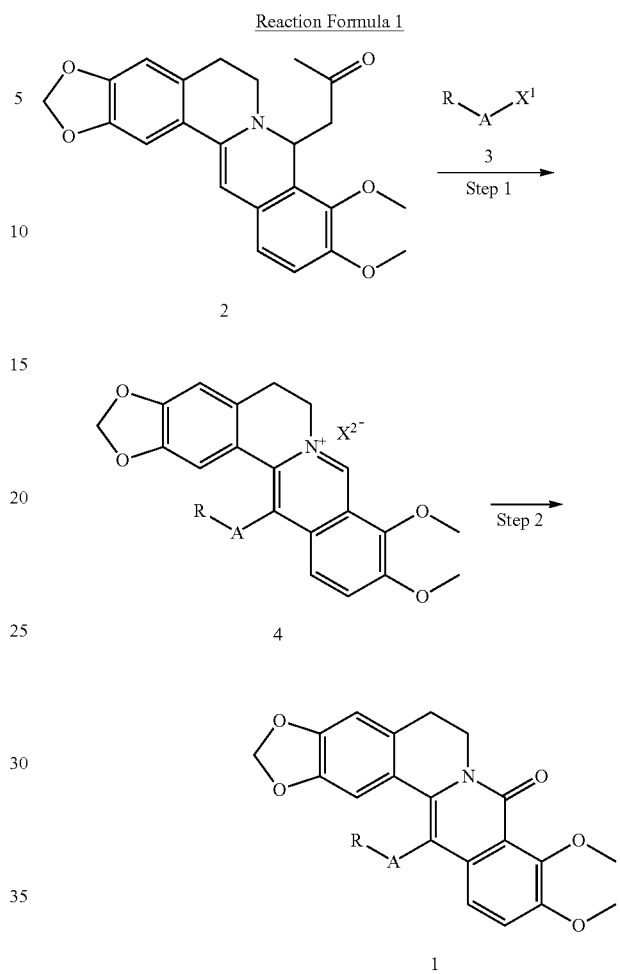

wherein in reaction formula 1, A and R are independently defined in claim 1;
and $X^1$ and $X^2$ are halogens.

4. The method of claim 3, wherein step 2 is composed of the following steps as shown in reaction formula 2:
preparing the compound represented by formula 5 via reduction reaction of the compound represented by formula 4 (step A); and
preparing the compound represented by formula 1 via oxidation reaction of the compound represented by formula 5 obtained in step A (step B):

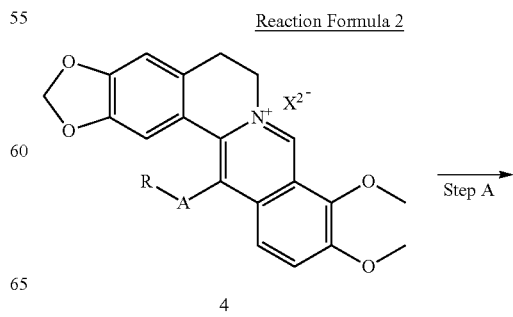

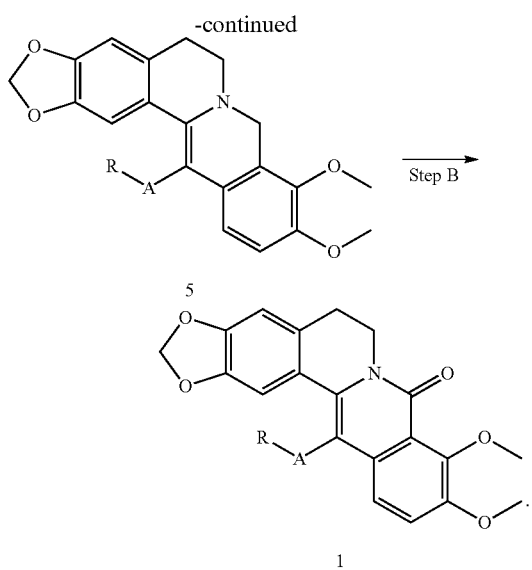

5. A method for treating diseases associated with the activity of NFAT5 comprising the step of administering an effective dose of the 8-oxoprotoberberine derivative or the pharmaceutically acceptable salt thereof of claim 1 to a subject, wherein the disease is arthritis or an auto-immune disease selected from the group consisting of systemic scleroderma, lupus erythematosus, atopic dermatitis, Behcet's disease, Sjogren's syndrome, multiple sclerosis, and Graces' hyperthyroidism.

6. The method of claim 5 wherein the 8-oxoprotoberbeing derivative is one or more compounds selected from the group consisting of:

—-ethyl-9,10-dimethoxy-8-oxo-6,8-dihydro-5H-[1,3]dioxolo[4,5-g]isoquinolino[3,2-a]isoquinoline-13-carboxylate;

9,10-dimethoxy-8-oxo-6,8-dihydro-5H-[1,3]dioxolo[4,5-g]isoquinolino[3,2-a]isoquinoline-13 -carboxylic acid;

9,10-dimethoxy-8-oxo-6,8-dihydro-5H-[1,3]dioxolo[4,5-g]isoquinolino[3,2-a]isoquinoline-13   -carboxamide; and N-(2-fluorophenyl)-9,10-dimethoxy-8-oxo-6,8-dihydro-5H-[1,3]dioxolo   [4,5-g]isoquinolino[3,2-a]isoquinoline-13-carboxamide.

7. The method of claim 5 wherein the arthritis is rheumatoid arthritis.

* * * * *